US008874187B2

(12) United States Patent
Thomson et al.

(10) Patent No.: US 8,874,187 B2
(45) Date of Patent: Oct. 28, 2014

(54) DYNAMIC TRACKING OF MOVING TARGETS

(75) Inventors: Euan Thomson, Los Gatos, CA (US); John Robinson Dooley, Castro Valley, CA (US); Gopinath Kuduvalli, San Jose, CA (US); James Wang, Palo Alto, CA (US); Eric Earnst, Saratoga, CA (US); Chris Raanes, Portola Valley, CA (US)

(73) Assignee: Accuray Inc., Sunnyvale, CA (US)

( * ) Notice: Subject to any disclaimer, the term of this patent is extended or adjusted under 35 U.S.C. 154(b) by 2031 days.

(21) Appl. No.: 11/890,881

(22) Filed: Aug. 7, 2007

(65) Prior Publication Data

US 2008/0039713 A1 Feb. 14, 2008

(51) Int. Cl.
*A61B 5/05* (2006.01)
*A61B 6/03* (2006.01)
*A61B 6/00* (2006.01)
*A61N 5/10* (2006.01)
*A61B 19/00* (2006.01)
*A61B 5/113* (2006.01)
*A61B 17/00* (2006.01)

(52) U.S. Cl.
CPC ........... *A61B 19/5244* (2013.01); *A61N 5/1067* (2013.01); *A61B 6/037* (2013.01); *A61N 5/1037* (2013.01); *A61N 5/1064* (2013.01); *A61B 2019/505* (2013.01); *A61N 2005/1055* (2013.01); *A61B 19/52* (2013.01); *A61B 6/032* (2013.01); *A61B 2019/207* (2013.01); *A61B 5/113* (2013.01); *A61B 2019/524* (2013.01); *A61B 2019/5295* (2013.01); *A61N 2005/1052* (2013.01); *A61B 6/5217* (2013.01); *A61B 2019/5265* (2013.01); *A61B 2017/00694* (2013.01); *A61N 2005/1061* (2013.01); *A61N 5/1049* (2013.01); *A61N 2005/1062* (2013.01)
USPC ................ 600/407; 378/62; 378/63; 378/64; 378/65

(58) Field of Classification Search
CPC ... A61N 5/103; A61N 5/1037; A61N 5/1048; A61N 5/1049; A61N 5/1064; A61N 5/1067; A61N 5/1068; A61N 2005/1062
USPC ....................................... 378/62–65; 600/407
See application file for complete search history.

(56) References Cited

U.S. PATENT DOCUMENTS 5,207,223 A 5/1993 Adler
5,588,430 A 12/1996 Bova et al.

(Continued)

FOREIGN PATENT DOCUMENTS

CN 1230878 A 10/1999
JP A-2001-505082 4/2001

(Continued)

OTHER PUBLICATIONS

Keall et al. (4-Dimensional Computed Tomography Imaging and Treatment Planning) Seminars in Radiation Oncology, vol. 14, No. 1 Jan. 2004: pp. 81-90.*

(Continued)

*Primary Examiner* — Sanjay Cattungal
*Assistant Examiner* — Ellsworth Weatherby
(74) *Attorney, Agent, or Firm* — Lowenstein Sandler LLP

(57) ABSTRACT

Treatment targets such as tumors or lesions, located within an anatomical region that undergoes motion (which may be periodic with cycle P), are dynamically tracked. A 4D mathematical model is established for the non-rigid motion and deformation of the anatomical region, from a set of CT or other 3D images. The 4D mathematical model relates the 3D locations of part(s) of the anatomical region with the targets being tracked, as a function of the position in time within P. Using fiducial-less non-rigid image registration between pre-operative DRRs and intra-operative x-ray images, the absolute position of the target and/or other part(s) of the anatomical region is determined. The cycle P is determined using motion sensors such as surface markers. The radiation beams are delivered using: 1) the results of non-rigid image registration; 2) the 4D model; and 3) the position in time within P.

21 Claims, 17 Drawing Sheets

(56) References Cited

U.S. PATENT DOCUMENTS

| | | | |
|---|---|---|---|
| 5,727,554 | A | 3/1998 | Kalend et al. |
| 5,802,220 | A | 9/1998 | Black et al. |
| 6,038,284 | A | 3/2000 | Hernandez-Guerra et al. |
| 6,144,825 | A | 11/2000 | Park |
| 6,169,817 | B1 | 1/2001 | Parker et al. |
| 6,307,914 | B1 | 10/2001 | Kunieda et al. |
| 6,477,229 | B1 | 11/2002 | Grosser |
| 6,501,981 | B1 | 12/2002 | Schweikard et al. |
| 6,662,036 | B2* | 12/2003 | Cosman .................. 600/411 |
| 6,728,424 | B1 | 4/2004 | Zhu et al. |
| 6,728,850 | B2 | 4/2004 | Gotoh et al. |
| 6,965,847 | B2 | 11/2005 | Wessol et al. |
| 7,046,765 | B2 | 5/2006 | Wong et al. |
| 7,166,852 | B2 | 1/2007 | Saracen et al. |
| 7,187,792 | B2 | 3/2007 | Fu |
| 7,204,640 | B2 | 4/2007 | Fu |
| 7,231,076 | B2 | 6/2007 | Fu |
| 7,250,426 | B2 | 7/2007 | Konetzki et al. |
| 7,280,865 | B2 | 10/2007 | Adler |
| 7,327,865 | B2 | 2/2008 | Fu et al. |
| 7,578,816 | B2 | 8/2009 | Boveja et al. |
| 8,086,299 | B2 | 12/2011 | Adler et al. |
| 2002/0085668 | A1 | 7/2002 | Blumhofer |
| 2002/0193685 | A1 | 12/2002 | Mate et al. |
| 2003/0048868 | A1 | 3/2003 | Bailey et al. |
| 2003/0125622 | A1* | 7/2003 | Schweikard et al. ......... 600/437 |
| 2003/0195413 | A1* | 10/2003 | Rubin et al. ................. 600/411 |
| 2004/0005027 | A1 | 1/2004 | Nafstadius |
| 2004/0092815 | A1* | 5/2004 | Schweikard et al. ......... 600/425 |
| 2004/0116804 | A1 | 6/2004 | Mostafavi |
| 2004/0122311 | A1 | 6/2004 | Cosman |
| 2004/0254492 | A1 | 12/2004 | Zhang et al. |
| 2004/0254773 | A1 | 12/2004 | Zhang et al. |
| 2004/0260142 | A1 | 12/2004 | Lovoi |
| 2005/0049478 | A1 | 3/2005 | Kuduvalli |
| 2005/0054916 | A1 | 3/2005 | Mostafavi |
| 2005/0111738 | A1 | 5/2005 | Iizuka |
| 2005/0234327 | A1 | 10/2005 | Saracen et al. |
| 2006/0002601 | A1 | 1/2006 | Fu |
| 2006/0002615 | A1 | 1/2006 | Fu |
| 2006/0002630 | A1 | 1/2006 | Fu |
| 2006/0002632 | A1* | 1/2006 | Fu et al. ................... 382/294 |
| 2006/0074292 | A1 | 4/2006 | Thomson et al. |
| 2006/0093089 | A1 | 5/2006 | Vertatschitsch et al. |
| 2006/0274061 | A1 | 12/2006 | Wang et al. |
| 2007/0165779 | A1 | 7/2007 | Chen et al. |
| 2007/0286331 | A1* | 12/2007 | Keall et al. ..................... 378/8 |
| 2008/0049897 | A1 | 2/2008 | Molloy |
| 2008/0063299 | A1 | 3/2008 | Murai et al. |
| 2008/0300502 | A1* | 12/2008 | Yang et al. .................. 600/534 |

FOREIGN PATENT DOCUMENTS

| | | |
|---|---|---|
| JP | A-2003-530177 | 10/2003 |
| JP | 2008-514352 | 5/2008 |
| WO | WO9811822 | 3/1998 |
| WO | WO9816151 A1 | 4/1998 |
| WO | WO 02/17876 | 3/2002 |
| WO | WO 02/100485 | 12/2002 |
| WO | WO 03/003796 | 1/2003 |
| WO | WO 03/083779 | 10/2003 |
| WO | WO2004/044612 A2 | 5/2004 |

OTHER PUBLICATIONS

Zhang et al., Treatment plan optimization incorporating respiratory motion, Medical Physics, vol. 31, No. 6, Jun. 2004, pp. 1576-1586.*
Keall et al., Monte Carlo as a four-dimensional radiotherapy treatment-planning tool to account for respiratory motion, Phys. Med. Biol. 49 (2004) 3639-3648.*
Ding et al., Dose correlation for thoracic motion in radiation therapy of breast cancer, Medical Physics, vol. 30, No. 9, Sep. 2003, pp. 2520-2529.*
Brock et al., Technical note: Creating a four-dimensional model of the liver using finite element analysis, Med. Phys., 29, 7, Jul. 2002, pp. 1403-1405.*
Vedam et al., Predicting respiratory motion for four-dimensional radiotherapy, Med. Phys., 31, 8, Aug. 2004, pp. 2274-2283.*
Whyte et al. Stereotactic Radiosurgery for Lung Tumors: Preliminary Report of a Phase I Trial, Ann. Thorac. Surg., 2003;75:1097-101.*
Murphy et al., Patterns of Patient Movement During Frameless Image Guided Radiosurgery, Int. J. Radiation Oncology Biol. Phys., vol. 55, No. 5, pp. 1400-1408, 2003.*
Schweikard et al., Robotic Motion Compensation for Respiratory Movement during Radiosurgery, Computer Aided Surgery 5:263-277 (2000).*
Murphy (An automatic six-degree-of-freedom image registration algorithm for image-guided frameless stereotaxic radiosurgery), Med. Phys. 24 (6), Jun. 1997, 857-866.*
U.S. Appl. No. 11/479,358, Office Action mailed Jan. 21, 2011.
U.S. Appl. No. 10/957,467, Restriction Requirement mailed Jul. 27, 2007.
U.S. Appl. No. 10/957,467, Restriction Requirement mailed Oct. 31, 2007.
U.S. Appl. No. 10/957,467, Office Action mailed May 14, 2008.
U.S. Appl. No. 10/957,467, Final Office Action mailed Nov. 13, 2008.
U.S. Appl. No. 10/957,467, Office Action mailed Jun. 10, 2009.
U.S. Appl. No. 10/957,467, Final Office Action mailed Mar. 2, 2010.
PCT International Preliminary Report on Patentability, PCT/US2005/030081 filed Aug. 22, 2005, mailed Apr. 26, 2007.
PCT Search Report, PCT/US05/30081 filed Aug. 22, 2005, mailed Mar. 29, 2007.
PCT Written Opinion of the International Searching Authority, PCT/US05/30081 filed Aug. 22, 2005, mailed Mar. 29, 2007.
Paul Keall: "4-Dimensional Computed Tomography Imaging and Treatment Planning" Seminars in Radiation Oncology, Saunders, Philadelphia, PA, US, vol. 14, No. 1, Jan. 1, 2004, pp. 81-90, XP002461023, ISSN: 1053-4296.
Brock K. K. et al.: "Inclusion of organ deformation in dose calculations", Medical Physics, AIP, Melville, NY, US, vol. 30, No. 3, Mar. 1, 2003, pp. 290-295, XP012011997, ISSN: 0094-2405.
Extended Search Report, EP Application No. 05791522.5, dated Aug. 17, 2009, 9 pages.
Jason C. Crane et al., "Grid enabled magnetic resonance scanners for near real-time medical image processing", Journal of Parallel and Distributed Computing, vol. 66, Issue 12, Dec. 2006, 3 pages.
Chinese Patent Application No. 200580041043.3, First Office Action issued Dec. 19, 2008, 10 pages.
Chinese Patent Application No. 200580041043.3, Second Office Action issued Aug. 28, 2009, 5 pages.
U.S. Appl. No. 11/479,358, Office Action dated Apr. 26, 2010, 16 pages.
Coste-Maière, È., "Robotic Whole Body Stereotactic Radiosurgery: Clinical Advantages of the CyberKnife® Integrated System," The International Journal of Medical Robotics +Computer Assisted Surgery, 2005, www.roboticpublications.com, pp. 28-39.
English Translation of Chinese Patent Application No. 200580041043.3, Office Action dated Jan. 13, 2011, 6 pages.
Chinese Patent Application No. 200580041043.3, Office Action dated Jan. 13, 2011, 4 pages.
English Translation of Japanese Patent Application No. 2007-534595 Office Action dated Dec. 6, 2010, 3 pages.
Japanese Patent Application No. 2007-534595 Office Action dated Dec. 6, 2010, 4 pages.
Bibliographic data for Japanese Patent Application No. JP2001505082 (T), publication date Apr. 17, 2001.
Bibliographic data for Japanese Patent Application No. JP2003530177 (T), publication date Oct. 14, 2003.
Vedam et al. (Oct. 2001). "Determining parameters for respiration-gated radiotherapy," Med. Phys. vol. 28, No. 10, 2139-2146.
U.S. Appl. No. 10/957,467, Final Office Action mailed Nov. 27, 2013.

(56) References Cited

OTHER PUBLICATIONS

U.S. Appl. No. 10/957,467, Final Office Action mailed Mar. 25, 2014.
U.S. Appl. No. 12/963,896, Final Office Action mailed Feb. 24, 2014.
Office Action for Chinese Patent Application No. 201110200098.1, mailed Mar. 1, 2013.
Office Action for European Patent Application No. 05791522.5 mailed Apr. 12, 2013.
Paul J. Keall et al., "Four-dimensional radiotherapy planning for DMLC-based respiratory motion tracking", Med. Phys. 32 (4), Apr. 2005, pp. 942-951.
Rietzel et al., Four-Dimensional Image-Based Treatment Planning: Target Volume Segmentation and Dose Calculation in the presence of Respiratory Motion, International Journal of Radiation Oncology Biology and Physics, vol. 61, Issue 5, Apr. 1, 2005, pp. 1535-1550.

* cited by examiner

|   |   |   |
|---|---|---|
| 1 | 2 | 3 |
| 4 | 5 | 6 |
| 7 | 8 | 9 |
|   |   |   | d2=(d1+d3)/2
d4=(d1+d7)/2
d5=(d1+d3+d7+d9)/4
d6=(d3+d9)/2
d8=(d7+d9)/2

FIG. 12

DYNAMIC TRACKING OF MOVING TARGETS

REFERENCE TO RELATED APPLICATION

This application is a divisional of application Ser. No. 10/957,467, filed Sep. 30, 2004, which is hereby incorporated by reference.

BACKGROUND

In some medical applications, it may be necessary to dynamically track targets that move with time. For example, in radiosurgery it may be desirable to dynamically track tumors and/or lesions in the human body that move with respiration and/or heartbeat. In radiosurgery, accurate trajectories of the radiation beams through the patient anatomy to the lesion or tumor being treated can be critical, in order to achieve the radiation dose distribution that was computed during treatment planning time. For regions of the human anatomy that move, for example due to breathing or heartbeat, it is important to take such motions into consideration, when computing the effect of the motion on the treatment plan being generated. Dynamic tracking may also be useful in applications other than radiosurgery in which parts of the anatomy move, due to breathing, heartbeat, or any other type of motion.

Fiducial markers have been used in the past, in order to track moving regions of the anatomy. Fiducials-based tracking can be difficult for a patient, for a number of reasons. For example, high accuracy tends to be achieved by using bone-implanted fiducial markers, but less invasive techniques such as skin-attached markers or anatomical positions tend to be less accurate. Implantation of fiducials into a patient is generally painful and difficult, especially for the C-spine, the implantation process for which may frequently lead to clinical complications.

In some methods that use gating to handle anatomical motion, dynamic tracking may be achieved by establishing a relationship between internally implanted fiducials, and externally placed markers that are tracked in real time. These methods do not take into account the non-rigid motions and deformations of the surrounding anatomy, as a function of the motion cycle.

A method and system that address these deficiencies are thus desirable. In particular, it is desirable to provide a reliable and efficient method and system for dynamically tracking moving targets.

SUMMARY

A method and system are presented for dynamically tracking one or more targets within an anatomical region so that desired doses of therapeutic radiation can be delivered to the targets, while the anatomical region is undergoing motion. The targets may be tumors or lesions, for example. The anatomical region may include one or more reference structures, in addition to the targets. The locations of the targets within the moving anatomical region are determined relative to the reference structures, while taking into account the deformation that the anatomical region undergoes during its motion. The deformation of the anatomical region includes non-rigid deformations, as well as rigid deformations.

In one embodiment, the motion of the anatomical region may be periodic. Examples of such periodic motion may include, for example, respiration or heartbeat. The periodic motion may be characterized by a periodic cycle P. In other embodiments, the motion of the anatomical region may be aperiodic motion, in which the cycle P may change over time, or for which no cycle P is defined. Throughout this patent application, the terms "periodic motion" and "periodic motion with cycle P" include periodic motions having a time-varying period P(t). In other words, the terms "periodic motion" and "periodic motion with cycle P" should be understood as being descriptive of, and referring to, the changing nature of the motions in the human anatomy.

In one embodiment, dynamic tracking of a periodic motion with cycle P is accomplished by constructing a 4D (four dimensional) mathematical model that describes the non-rigid deformation and non-rigid motion of the anatomical region, as a function of the relative position in time within the cycle P. The 4D mathematical model may be constructed by generating a plurality of images (including but not limited to CT images) $I_j$ (j=1, . . . , p) of the anatomical region, where each image is taken at one of a succession of time points $t_j$ (j=1, . . . p) within the cycle P. The continuous non-rigid deformation of the anatomical region, as a function of the cycle P, is mathematically modeled by morphing a CT image, acquired at one instant in time, into another CT image acquired at a subsequent instant in time. The 4D mathematical model relates the 3D (three dimensional) locations of the skeletal structures with the 3D locations of the targets, as a function of the instant in the cycle P (which may be, for example, a breathing cycle or a heartbeat cycle).

In one embodiment, the 4D mathematical model of the non-rigid deformation is used by a treatment plan generator to generate a radiation dose distribution that prescribes a desired amount of the therapeutic radiation to be delivered, in real time, to the targets within the moving anatomical region. The radiation dose distribution accounts for the non-rigid deformation of the moving anatomical region during its periodic motion.

The cycle P for the periodic motion may be determined for example by dynamically tracking motion sensors (such as surface markers or LEDs (light emitting diodes), by way of example) attached to the skin or exterior surface of the anatomical region. The relative position within the motion cycle P of any desired time point, including the time point $t_j$ at which the j-th image $I_j$ was taken, can be determined in this way.

In this patent, the term "real time" refers to a time scale that is substantially simultaneous to the actual radiation treatment and delivery. For example, tracking that occurs at a speed of at least several Hz or higher falls within the time scale described as "real time" in this patent. In this patent, the term "near real time" refers to a time scale that is slower than the time scale referred to as "real time," for example by about one or more orders of magnitude. For example, events occurring at a speed of less than about once a second falls within the time scale described as "near real time" in this patent.

In one embodiment, the near real time locations of the reference structures are determined by performing fiducial-less tracking of the reference structures. A set of DRRs are generated from the CT image data, using the same beam projection geometry as is used to acquire the live x-ray images. The live x-ray images, acquired intra-operatively in near real time, are registered with the DRRs (digitally reconstructed radiographs). In one embodiment, a non-rigid image registration algorithm may be used, in which the non-rigid transformation parameters are derived from a 3D full motion field. The full motion field may be constructed by estimating many local motion vectors. In one embodiment, multi-level block matching may be used in the non-rigid image registration algorithm, in conjunction with a similarity measure based on pattern intensity. In one embodiment, hierarchical mesh motion estimation may be performed.

In one embodiment, the locations of the targets can be determined in real time, by correlating the known near real time locations of the reference structures, which were determined using non-rigid image registration, with the target locations that are being sought, using the 4D mathematical model that describes how the locations of the targets are related to the locations of the reference structures, as a function of the relative position in time within the cycle P. The information from the motion sensors can be used to determine the relative position within the cycle P of any desired time point.

In one embodiment, radiation treatment is delivered to the real time locations of the targets, in accordance with the radiation dose distribution generated by the treatment planning generator. The radiation beam delivery can be synchronized to the instant in breathing cycle determined in the treatment planning.

BRIEF DESCRIPTION OF THE DRAWINGS

FIG. 12 schematically illustrates the passing on of node estimation, from a coarse mesh resolution level onto a finer mesh resolution level.

DETAILED DESCRIPTION

Figure 1:
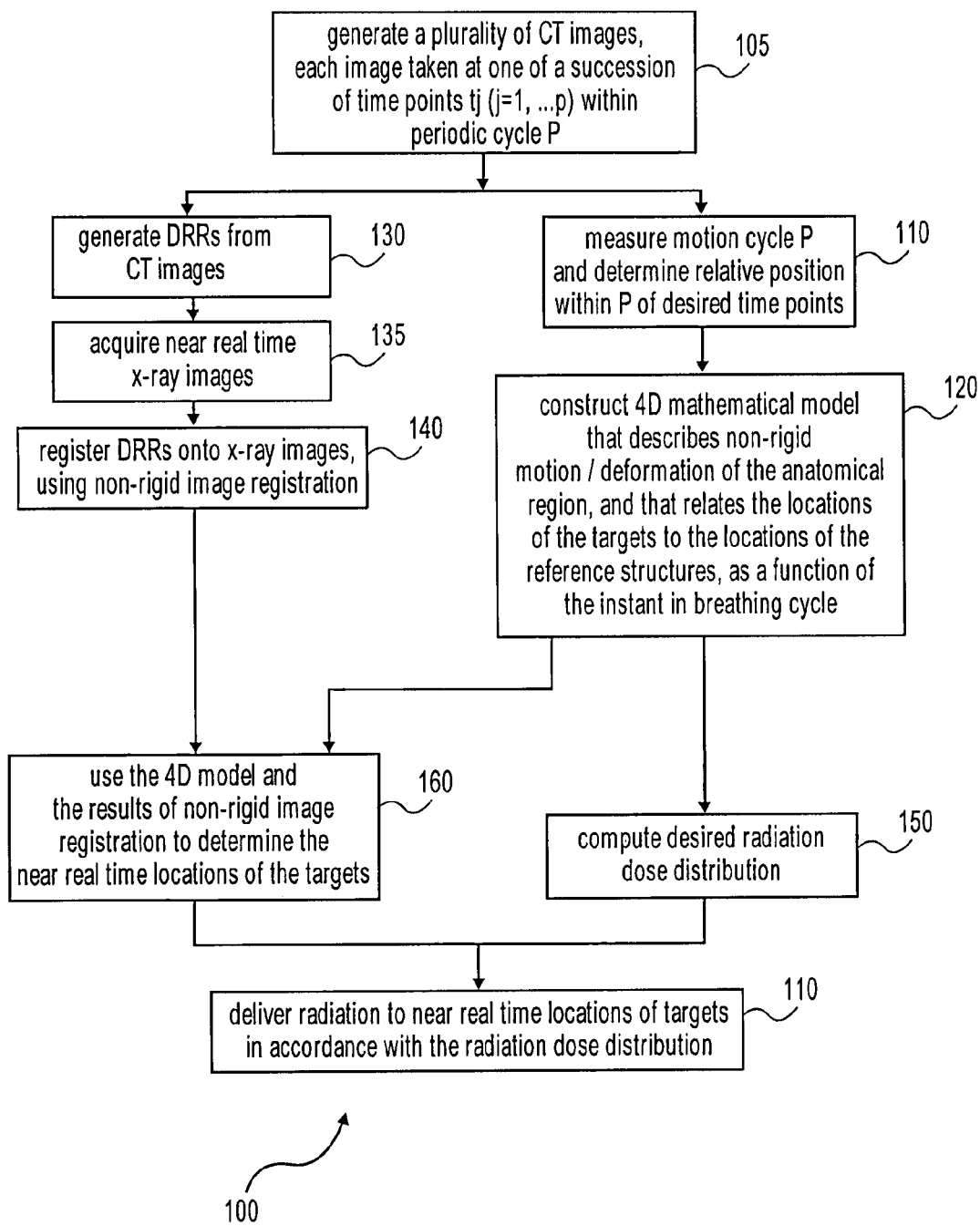
FIG. 1 provides a schematic flow chart of a method for dynamic fiducial-less tracking of moving targets.

A number of techniques are described for dynamically tracking tumors/lesions in the human body that is undergoing motion. The methods are of principal use in radiosurgery, but may also be useful in other applications where it may be necessary to dynamically track parts of the anatomy that move, for example because of respiration or heartbeat.

Some portions of the detailed description that follows are presented in terms of algorithms and symbolic representations of operations on data bits within a computer memory. These algorithmic descriptions and representations are the means used by those skilled in the data processing arts to most effectively convey the substance of their work to others skilled in the art. An algorithm is conceived to be a self-consistent sequence of acts leading to a desired result. These acts require physical manipulations of physical quantities. Usually, though not necessarily, these quantities may take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, it is appreciated that throughout the descriptions below, discussions that utilize terms such as "processing" or "computing" or "calculating" or "determining" or "displaying" or the like, refer to the actions and processes of a computer system, or a similar electronic computing device. The computer system manipulates and transforms data, represented as physical or electronic quantities within the computer system's registers and memories, into other data similarly represented as physical quantities within the computer system's memories or registers, or within other such information storage, transmission or display devices.

The methods and techniques described below can be implemented by an apparatus for performing the operations discussed below. Such an apparatus may be specially constructed for the required purposes, or it may comprise a general purpose computer, selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions. Each such computer readable storage medium may be coupled to a computer system bus.

The algorithms and displays presented herein are not inherently related to any particular computer or other apparatus. Various general purpose systems may be used with programs that are designed in accordance with the teachings below, or it may prove convenient to construct a more specialized apparatus to perform the requisite methods and techniques. For example, any of the methods described below can be implemented in hard-wired circuitry, or by programming a general purpose processor, or by any combination of hardware and software. One of skill in the art will appreciate that the methods and techniques described below can be practiced with a wide variety of computer system configurations, including hand-held devices, multiprocessor systems, microprocessor-based or programmable consumer electronics, network PCs, minicomputers, mainframe computers, and the like. The methods and techniques described below can also be practiced in distributed computing environments where tasks are performed by remote processing devices that are linked through a communications network.

The methods and systems described below may be implemented using computer software. Computer software may be referred to using different terms, for example a program, a procedure, or an application. If written in a programming language conforming to a recognized standard, sequences of instructions designed to implement these methods and systems can be compiled for execution on a variety of hardware platforms and for interface to a variety of operating systems. Also, these methods and systems are not described with reference to any particular programming language. It will be appreciated that a variety of programming languages may be used to implement the teachings of the invention as described herein. Furthermore, it is common in the art to speak of software, in one form or another, as taking an action or causing a result. Such expressions are merely a shorthand way of saying that the execution of the software by a computer causes one or more processors in the computer to perform an action or produce a result.

FIG. 1 provides a schematic flow chart 100 describing the dynamic fiducial-less tracking of moving targets. The targets are located within an anatomical region. The targets may be tumors or lesions, for example, or organs of interest. The anatomical region typically includes one or more reference structures, in addition to the targets. In one embodiment of the dynamic tracking method and system, the reference structures may be skeletal (i.e. bony) structures. In another embodiment, the reference structures may be other natural anatomical structures, including but not limited to cartilages or other (typically rather dense) organs. In yet another embodiment, the reference structures may be artificial structures, for example fiducials or surgical hardware.

As mentioned earlier, throughout this description the term "periodic motion with cycle P" should be understood as including periodic motions in which the cycle P of the periodic motion, as well as the amplitude and waveform of the motion, change with time, In other words, the term "periodic motion" or "periodic motion with cycle P" should be understood as also referring to the changing nature of the motions in the human anatomy.

As mentioned earlier, the anatomical region may undergo a deformation (which may be a non-rigid deformation) during its motion. While in the embodiment illustrated in FIG. 1, the anatomical region is described as moving periodically while undergoing a non-rigid deformation, any other type of motion (e.g. aperiodic motion) and any type of deformation of the anatomical region may be tracked, using the method and system described in this patent.

In overview, in the embodiment illustrated in FIG. 1 the locations of the targets, within the periodically moving and non-rigidly deforming anatomical region are determined, in steps 105-160. A radiation dose distribution is computed that results from a substantially continuous delivery of radiation through the non-rigidly moving and deforming anatomical region. Finally, in step 170, radiation is delivered in real time to the targets, in accordance with the computed radiation dose distribution.

As a first step, a set of CT images $I_j$ (j=1, ... p) are acquired in step 105, each CT image taken at one of a succession of time points $t_j$ (j=1, ... p) within the cycle P. In step 110, the cycle of the periodic motion (e.g., the respiratory cycle or the heartbeat cycle) is established, for example by dynamic tracking of markers or other sensors attached to the skin of the anatomical region.

In step 120, a 4D (3D+time) mathematical model is constructed from these CT scans and from the motion cycle information obtained from the sensors. The mathematical model describes a non-rigid motion and deformation of the anatomical region as it undergoes its periodic motion (e.g. respiration), as a function of the instant in the motion cycle P. The 4D mathematical model relates the locations of the targets to the locations of the reference structures, as a function of the relative position in time within the cycle P, within the periodically moving anatomical region. More generally, this 4D model may describe the 3D+time relationship between a part or parts of the anatomy, and a target to be tracked for radiosurgery, as a function of the instant in time in the breathing cycle.

Next, in steps 130, 135, and 140 the absolute position of a part or parts of the anatomy is determined, using x-ray imaging and 2D-to-3D image registration. In these steps, the locations of the reference structures and/or the targets are determined in near real time, by fiducial-less tracking of the reference structures and/or targets using a non-rigid image registration algorithm.

As explained earlier, in this patent the term "real time" refers to a time scale that is substantially simultaneous to the actual radiation treatment and delivery. In just one exemplary embodiment, intra-operative real-time tracking of a target may be implemented using optical markers which track at about a 30 Hz rate, and using a model which updates its predictions at about a 80 Hz rate. This is intended to be an illustrative example only, and real time tracking may occur at a wide range of different tracking speeds, generally higher than about 1 Hz. The term "near real time" refers to a time scale that is slower, for example by about one or more orders of magnitude, than the time scale described by the term "real time." As an example, the time scale for acquiring x-ray images, which may range from about a fraction of a second to about several seconds, will be described as "near real time."

A set of DRRs of the anatomical region are generated, in step 130, from the CT images acquired in step 105. In step 135, live x-ray projection images of the anatomical region are acquired. In step 140, the DRRs of the reference structures are registered with the near real time x-ray images of the reference structures.

Step 150 describes 4D treatment planning, in which a radiation dose distribution is computed that results from continuous beam delivery through the non-rigidly moving and deforming anatomical region. In this step, the radiation beam trajectories are determined, using the knowledge (obtained in step 140) of the absolute locations of the reference structures, and using the 4D model that relates the reference structures to the instant in breathing cycle (as determined using information from the sensors), and to the targets whose locations are being tracked.

In step 160, the target locations are determined. In one embodiment, the 4D mathematical model may be used, together with the absolute positions of the skeletal structures as determined by fiducial-less tracking, and the information obtained from the sensors regarding the motion cycle, to determine the target locations. In an alternative embodiment, the target locations may be determined by 2D/3D non-rigid image registration, during which the DRRs (generated during the treatment planning stage) are registered onto near real time x-ray images. Finally, in step 170, radiation is delivered to the targets in accordance with the radiation dose distribution generated through 4D treatment planning.

Figure 2:
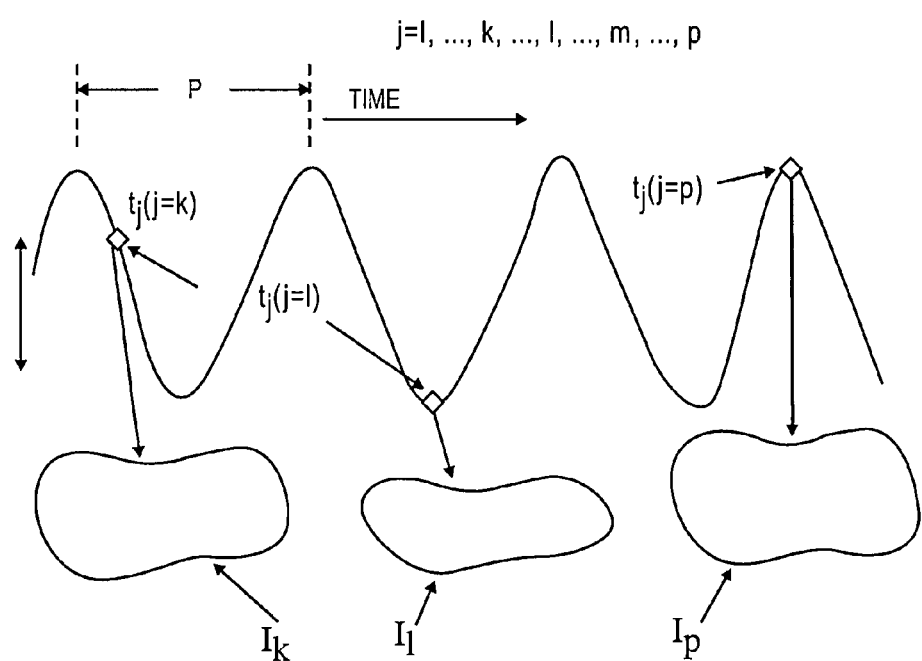
FIG. 2 schematically illustrates the acquisition of pre-operative images (e.g. 3D CT scans) of a moving target within a patient's anatomy, taken at different times points within a breathing cycle of the patient.

FIG. 2 schematically illustrates the acquisition of pre-operative images (e.g. 3D CT scans) of a moving target within a patient's anatomy. In the illustrated embodiment, the target moves due to breathing motion of the patient. While the illustrated embodiment shows 3D CT scans, any other type of 3D scans may be performed, including but not limited to 3D MRI (magnetic resonance imaging) scans, 3D PET (positron emission tomography) scans, and 3D ultrasound scans. In the illustrated embodiment, a set of CT scans are taken at different times points $t_j$ (j=1, . . . , k, . . . , l, . . . , m, . . . , p) within a breathing cycle P of the patient. In the illustrated embodiment, $t_1 < t_k < t_l < t_m < t_p$. The time points $t_j$ correspond to different epochs in the patient breathing cycle. The cycle P is monitored by an external sensor, e.g. a breathing sensor. For example, a surface marker (such as an LED) or a similar device may be attached to the skin. In embodiments in which the target undergoes motions other than respiration, different types of sensors (e.g. a cardiac monitor when heartbeat is being monitored) may be used.

In the illustrated embodiment, the CT images are taken at time points $t_k$, $t_l$, and $t_p$, respectively. The epochs or time points within the breathing cycle P are preferably chosen to substantially encompass the overall dynamic range of the periodic motion. For example, in one embodiment, the time points may include: a time point $t_l$ corresponding to a trough of the cycle P; a time point $t_p$ corresponding to a peak of the cycle P; and a third time point $t_k$ disposed at an intermediate location between the peak and the trough of the cycle P. In other embodiments, the time points selected for taking the CT images may include more than the three time points $t_l$, $t_p$, and $t_k$ described above.

From this set of CT studies, a 4D mathematical model is constructed that morphs the CT image acquired at one instant or time point in the motion cycle into another CT image acquired at a subsequent instant or time point in the motion cycle, providing a model for the continuous non-rigid deformation of the anatomy as a function of the motion cycle. In image processing, it is well known in the art to morph one image into another image, and to describe this in terms of a mathematical model. Any standard software and/or algorithms that are known and may be commercially available can be used.

In one embodiment, the 4D mathematical model constructed from the set of CT images shown in FIG. 2 is used for 4D treatment planning, i.e. to compute the dose distributions resulting from a continuous radiation beam delivery through the non-rigidly moving anatomy, taking into account the non-rigid motion and deformation of the treatment targets as a function of the position in time within the motion cycle. In this embodiment, 4D treatment planning consists of two parts: a) creating a mathematical model for the non-rigid deformations of the anatomy as a function of the instant in the motion cycle, as described above; and b) using the mathematical model to compute the dose distributions resulting from continuous radiation beam delivery through the non-rigidly moving anatomy.

In order to compute the desired radiation dose distributions, the beam trajectories are initially defined with respect to a nominal patient coordinate system. In one embodiment, the nominal patient coordinate system may be chosen to orient with respect to one of the several CT images illustrated in FIG. 2 and acquired to cover the motion cycle. Different orientations may be chosen in other embodiments. In one embodiment, each radiation beam is turned on from the time corresponding to the point in time in which each CT image was taken, and remains on for a duration selected to give the desired dose distribution. The dose absorption is calculated as a function of time from the initial time point, taking into account the non-rigid deformations of the patient anatomy.

In one embodiment, the 4D mathematical model relates the 3D locations of one or more reference structures with the 3D locations of the target, as a function of the instant in the motion cycle. In the 4D model, one or more of the selected reference structures may be stationary with respect to the motion cycle, while others of the selected reference structures may undergo non-rigid motion with respect to the motion cycle.

Figure 3:
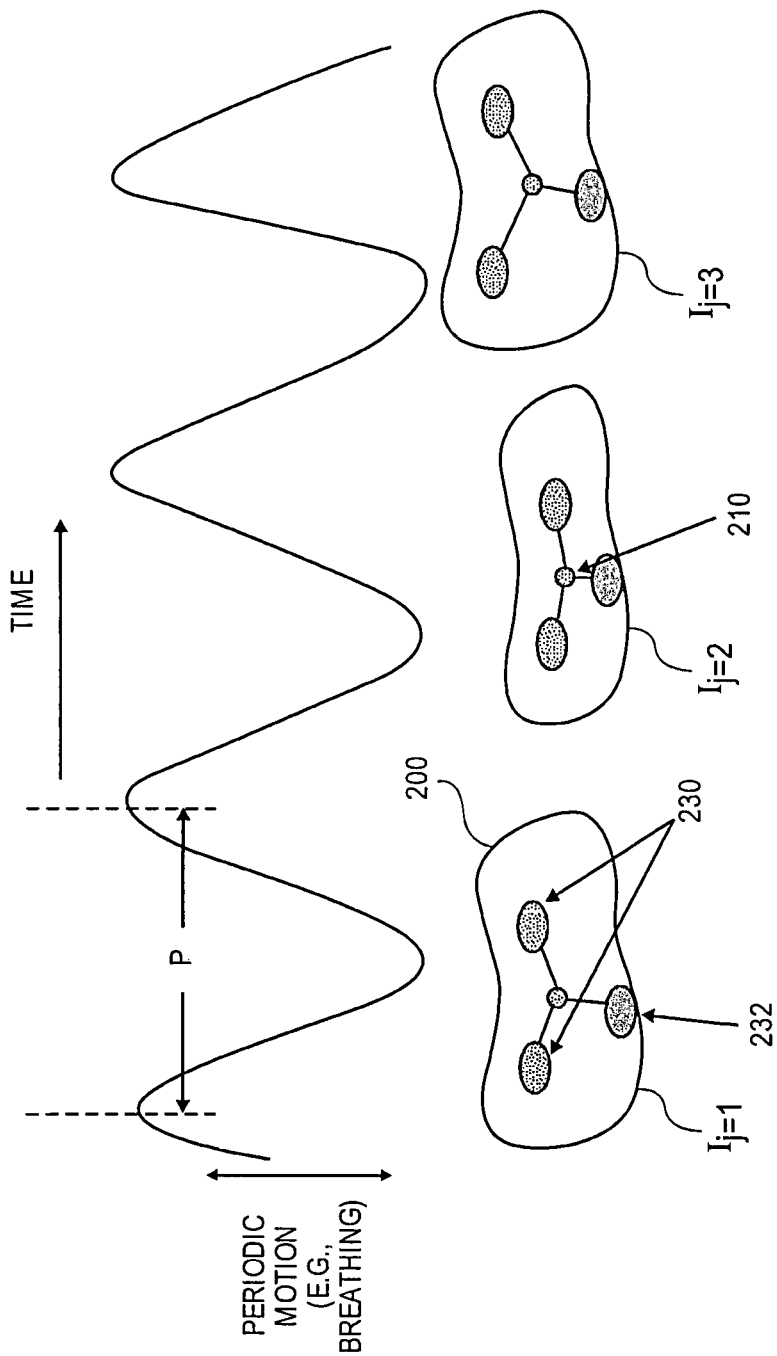
FIG. 3 schematically illustrates the tracking of the 3D motion of the target as a function of the breathing cycle of a patient, using one of: a) a rigid reference structure that does not move with breathing; and b) multiple reference structures that themselves move with breathing.

FIG. 3 schematically illustrates the tracking of the 3D motion of the target as a function of the motion cycle of a patient, using one of: a) a substantially rigid reference structure that is substantially stationary throughout the motion of the patient; and b) multiple reference structures that themselves move with the motion of the patient. Two kinds of models are possible: (a) 3D motion of the target (tumor/lesion) as a function of the motion cycle, with reference to a substantially rigid reference structure that is substantially stationary (including but not limited to vertebral structures) or (b) 3D motion of the target (e.g. tumor/lesion) as a function of the motion cycle, with reference to multiple reference structures that themselves move, along with the periodic motion of the anatomical region.

In the embodiment illustrated in FIG. 3, the target 210 moves within an anatomical region 200 because of the periodic motion of the anatomical region 200. The reference structures are illustrated using reference numeral 230 and 232. The reference structures 230 themselves move with breathing. On the other hand, reference structure 232 is a substantially rigid reference structure that does not move with the breathing or other periodic motion of the anatomical region 210.

The 3D location and orientation of the multiple skeletal structures enable vectors to be drawn that point from each skeletal structure to the tumor or lesion. A model that describes the 3D motion of the tumor/lesion as a function of the breathing cycle, with reference to a rigid skeletal structure (such as the skeletal structure indicated in FIG. 3 using reference numeral 210) that itself does not move with respect to breathing, may be used for example in conjunction with the vertebral structures for a patient lying supine for treatment, which is a practical example of such a non-moving skeletal structure. In another model, in which reference is made to rigid skeletal structures that themselves move with breathing, the 3D motion of the tumor/lesion can be described as a compound function of 1) the breathing cycle and the 2) location of multiple skeletal structures which themselves move with breathing.

Once the relationship between the locations of the reference structures and the locations of the target is determined by the 4D model, as a function of the point in time within the periodic motion cycle, the absolute position of the reference structures is determined in near real time. In one embodiment, this is accomplished by 1) generating DRRs of the reference structures from the 3D CT images, which were shown in FIG. 2 and which were used to generate the 4D mathematical model; 2) taking "live" or near real-time x-ray images of the reference structures; and then 3) performing non-rigid image registration between the live x-ray images and the DRRs. Once the locations of the reference structures are determined using non-rigid image registration, the locations of the targets can be easily determined using the 4D mathematical model described above.

Figure 4:
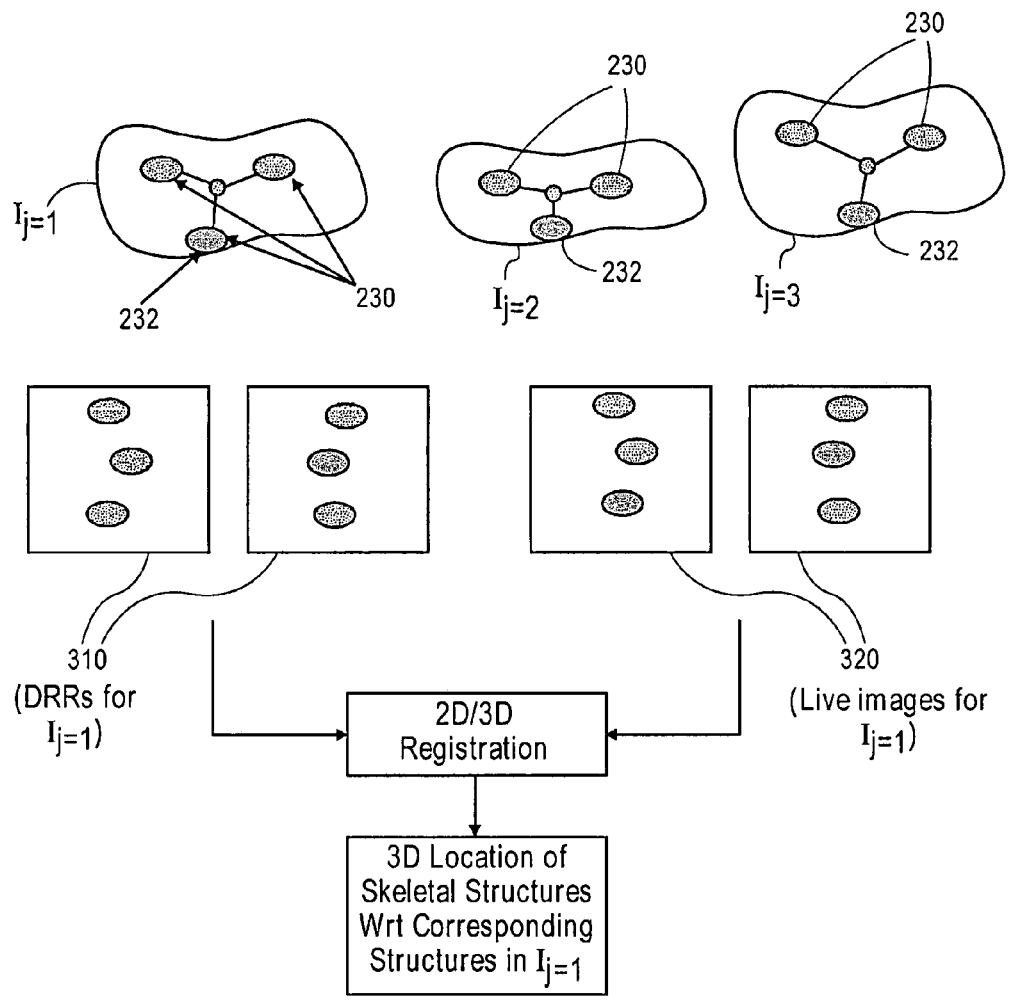
FIG. 4 schematically illustrates fiducial-less tracking of a moving target during delivery of treatment radiation, by registering 2D near real time x-ray images of the target with DRRs generated from a pre-operative 3D scan taken at a specific time point within the breathing cycle of the patient.

FIG. 4 schematically illustrates fiducial-less tracking of reference structures. In one embodiment, this fiducial-less tracking is performed by registering 2D near real time x-ray images of the target with DRRs generated from a pre-operative 3D scan taken at a specific time point within the motion cycle of the patient. The position and orientation of the reference structures in the patient anatomy (at the time of treatment delivery) can be tracked with respect to the corresponding structures in one of the CT studies, using a 2D to 3D registration methods. In one embodiment, a non-rigid 2D/3D image registration is performed, described in detail below.

As a first step in the 2D/3D non-rigid image registration process, a library of DRRs is generated for the projection geometry that will be used in the acquisition of live images at the time of treatment delivery. A pair of live (or "near real time") x-ray images of the patient is acquired during treatment delivery, using the same projection geometry as used for generating the DRRs. The CT images used to generate the DRRs will correspond to one of the epochs in the motion cycle, typically the same one with respect to which beams are assigned to during treatment planning. The DRRs may be generated for several translations and orientations of the CT image, in order to cover the typical range of patient movements during treatment.

The acquired images are registered with the DRRs using a feature recognition algorithm that tracks the reference structures. The image registration algorithm (described in detail below) may be repeated for multiple reference structures, to give the position and orientation of each structure with respect to the corresponding structures in the CT study (from which DRRs are made). In one embodiment, the difference in imaging characteristics of the tumor or lesion or a nearby anatomical region may be enhanced further by using high-sensitivity x-ray detectors.

In one embodiment, the location of the tumor/lesion can be derived from the locations of the reference structures, determined by the non-rigid registration process. The location and orientation of multiple reference structures tracked using the fiducial-less algorithm are used to interpolate the location of the tumor/lesion, using their corresponding geometric relationships, as learned from the CT studies and the 4D model. In another embodiment, fiducial-less tracking is performed for the targets (e.g. tumors/lesions) themselves. If the target being tracked is sufficiently different in x-ray imaging characteristics relative to the surrounding tissue, the target itself can be directly tracked using the 2D-to-3D registration technique described below.

A non-rigid 2D-to-3D image registration technique that accounts for non-rigid deformations of the anatomy, and which uses anatomical reference structures instead of fiducials, is described below. While the non-rigid image registration algorithm described below is described in the context of skeletal structures, and in particular skeletal structures in the spinal region of the human anatomy, it should be understood that reference structures other than spinal skeletal structures may also be used with this non-rigid image registration algorithm.

The non-rigid image registration technique is also described in the following five co-owned patent applications: 1) U.S. patent application Ser. No. 10/880,486, entitled "Fiducial-less Tracking With Non-Rigid Image Registration"; 2) U.S. patent application Ser. No. 10/881,612, entitled "Motion Field Generation For Non-rigid Image Registration"; 3) U.S. patent application Ser. No. 10/881,209, entitled "ROI Selection In Image Registration"; 4) U.S. patent application Ser. No. 10/881,208, entitled "Image Enhancement Method and System For Fiducial-less Tracking of Treatment Targets"; 5) U.S. patent application Ser. No. 10/881,206, entitled "DRR Generation Using A Non-Linear Attenuation Model." All five patent applications, owned are incorporated by reference herein in their entireties.

Figure 5:
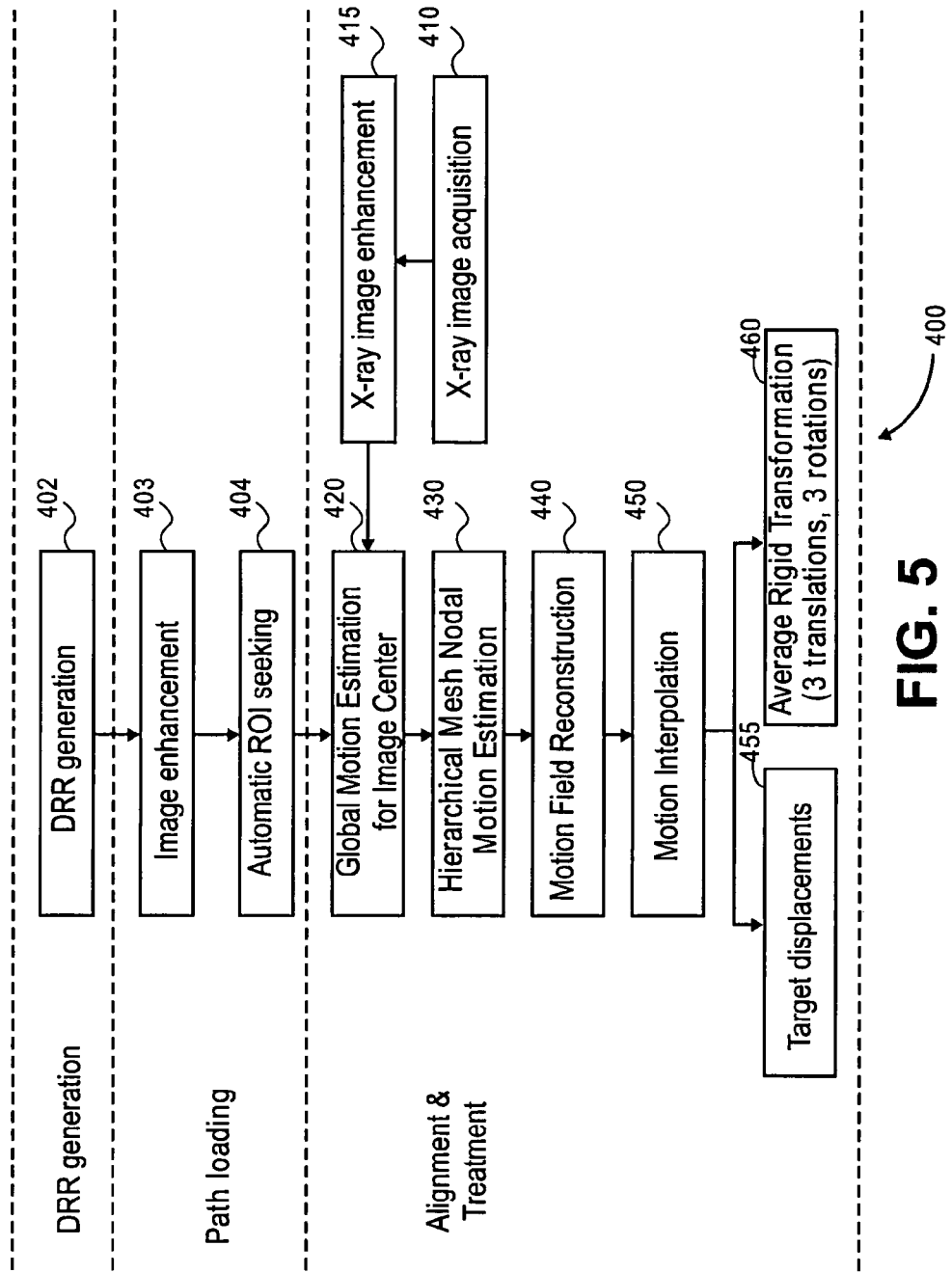
FIG. 5 illustrates a flowchart of a non-rigid image registration algorithm that may be used for a 2D/3D registration between pre-operative 2D DRRs, and intra-operative x-ray projection images.

FIG. 5 illustrates a flowchart 400 of a non-rigid image registration algorithm that may be used for a 2D/3D registration between 2D DRRs of an anatomical region, reconstructed from pre-operative CT scan data, and intra-operative, near real-time x-ray projection images of the target within the anatomical region. In particular, the DRR is reconstructed from CT scan data representative of a CT image $I_j$ taken at a specific time point $t_j$ within the periodic cycle P.

As a first step, 2D DRRs may be generated from pre-operative 3D scan data representative of a CT image $I_j$, in step 402. In one embodiment, the images for which non-rigid image registration is performed (i.e., DRRs and x-ray images) are discretized images each characterized by an array of pixels, each pixel having an associated pixel value representative of the intensity of the image at a surface unit area corresponding to the pixel.

In one embodiment, an improved DRR generation process can be implemented in step 402 to bring out the skeletal reference structures, which are usually not easily visible in the images, or even may be hidden. In step 402, the CT scan data are modified based on a non-linear attenuation model that emphasizes the skeletal structures and thus improves the quality of the DRRs. In step 403 in flowchart 400, an image enhancement technique may also be implemented for the DRRs. In this step, a top-hat filter is used to bring out the skeletal structures in the DRRs generated in step 402.

In the illustrated embodiment, image registration is performed in a selected region of interest (ROI) within the enhanced DRR, in order to improve efficiency. Accordingly, an ROI is defined in the DRR, in step 404, after enhancement of the DRRs. The ROI selection process performed in step 404 is based on image entropy, and is fully automatic so as not to require user interaction. Intra-operative 2D x-ray projection images are then generated, in near real time, in step 410. Image enhancement is performed on the x-ray images, in step 415, using a top-hat filter by analogy to step 403.

Non-rigid image registration is then performed between the enhanced x-ray images and the enhanced DRRs, within the ROI. In particular, a similarity measure is used to compare the pixel intensities in the x-ray images and the DRR images, in order to determine any change in the position and/or orientation and/or physiological deformation of the patient. In steps 420-450, a non-rigid deformation that describes real patient movement and body deformation is defined. To define the non-rigid deformation, a full motion field is constructed that is composed of many local motion fields, i.e. a plurality of locally estimated motion vectors. To estimate local motion at a given point of interest within the ROI, a similarity measure based on pattern intensity is used to compare pixel intensities.

A full motion field that is composed of many local motions may describe any desired non-rigid deformation. Further, a full motion field derived in this manner can account for non-rigid motions (translations and/or rotations) of the object, in addition to non-rigid deformations, between different image acquisitions of the object. In order to efficiently compute the local motion vectors at any point of interest within the ROI, hierarchical mesh motion estimation and multi-level block matching (performed in conjunction with an intensity-based similarity measure) are performed. These methods allow for a fast computation of the image registration algorithm 400. A smoothness constraint is imposed to reconstruct the motion field at mesh nodes in which mismatching occurred. The non-rigid transformation parameters for the non-rigid image registration are then computed from the full motion field.

In the embodiment illustrated in FIG. 5, the non-rigid deformations described by the full motion field occur in between the acquisition of the 3D CT scan data of a treatment target region in a patient, and the acquisition of the x-ray projection images of the target region. In step 420, a global translation of the entire image is first estimated. The estimated global translation is used as the initial estimate for all further local motion estimation. In the next step 430, mesh nodal motion estimation is performed, using a hierarchical mesh structure designed to estimate the local motion in multiple levels. In the next step 440, motion field reconstruction is performed for those mesh nodes in which a mismatch occurs. The reconstruction of the motion field is performed by imposing a smoothness constraint, which is based on the assumption that local motions are continuous, because of matter coherence. In step 450, the local motion vector at any desired point of interest is derived by interpolating from the nodal motions estimated for the mesh nodes that surround the point of interest. The full motion field is then constructed, using the local motion vectors derived for a plurality of desired points of interest.

In the final steps, shown as step 455 and step 460 in FIG. 5, the non-rigid transformation parameters are derived from the full motion field. In step 455, the target displacements are derived from the full motion field. In step 460, the average rigid transformation is derived from the full motion field.

The quality of DRR images relies on proper attenuation modeling, as well as a proper interpolation scheme for interpolation the CT numbers. In one embodiment, in step 402 (in the flowchart shown in FIG. 2), an improved x-ray attenuation model is formulated for fiducial-less tracking, so that the DRRs become more like the real x-ray projection images. A linear attenuation model is no longer assumed, and the CT numbers are modified in order to compensate for the above-mentioned a difference in the bone-to-tissue attenuation ratio. On the basis of many experiments conducted with patient clinical data, the following empirical equation was formulated to modify the original CT numbers:

$$C(x,y,z) = a\, C_0(x,y,z) e^{bC_0(x,y,z)} \quad (1)$$

where C(x,y,z) represents the modified CT number of a 3D CT voxel located at a point (x,y,z); a and b represent weighting coefficients;
and $C_0$(x,y,z) represents the unmodified CT number, based on a linear attenuation model, of a 3D CT voxel having a location (x,y,z).

The interpolation scheme used in one embodiment to improve the quality of DRRs is bi-linear interpolation. In this embodiment, bi-linear interpolation is performed in step 402, to integrate the CT numbers along the CT voxels that are encountered by each cast ray. In one embodiment, the bi-linear interpolation is followed by a 1-D polynomial interpolation over three voxel slices, for each voxel of interest. The three voxel slices include the voxel slice containing the voxel of interest, plus each adjacent voxel slice.

In some embodiments, fiducial-less tracking relies on skeletal reference structures (e.g. vertebral structures) that are usually not easily visible, or may even be hidden in the DRRs and in the x-ray projection images. Because such skeletal structures have to be registered, both the DRR and the x-ray images have to be enhanced to bring out the details of the vertebral structures and improve their visibility. In one embodiment, therefore, image enhancement is undertaken for both the DRRs and the x-ray projection images. In most thoracic and lumbar cases, the skeletal structures are not easily visible or even hidden in DRR and X-ray images. For these cases therefore, enhancement of the DRR and the x-ray images is necessary, in order to make registration at all possible. In cervical cases, the skeletal structures of spine are well visible in both the DRR and the x-ray images, but the details of the structures are still not clear. Accordingly, in cervical cases, the DRR and the x-ray images should be enhanced to improve the registration.

In the embodiment illustrated in FIG. 5, a top-hat filter is designed and used to enhance the x-ray images (step 415 in FIG. 5) and to enhance the DRR images (step 403 in FIG. 5). In particular, the skeletal structures in the images are enhanced, i.e., brought out, by applying a top hat filter operator to the pixels of the x-ray projection images and the DRR images. As known, a top hat filter is a nonlinear operator that finds the brightest pixels in two different size neighborhoods, then keeps the extreme values. In one embodiment, the top hat filter operates as follows: if the brightest value in the smaller neighborhood region is greater that the value in the larger neighborhood, by an amount determined by a user-entered threshold, then the pixel remains, otherwise it is eliminated. As a result of applying a top hat filter to the images, it is possible to locate features of interest.

In one embodiment, the top-hat filter is designed by using a weighted combination of image opening and closing with a certain structural element. The top hat filter operator is defined mathematically as follows:

$$f_e = f + w \times [f - \gamma_B(f)] - b \times [\varphi_B(f) - f] \quad (2)$$
$$= f + w \times WTH(f) - b \times BTH(f)$$

where $f_e$ represents the enhanced image, resulting from the application of the top hat filter operator to each pixel in the original image;
f represents the original image;
w and b represent weighting coefficients,
$\gamma_B$(f) represents a structural element for the opening of the original image f, and
$\varphi_B$(f) represents a structural element for the closing of the original image f.

In expression (2) above, WTH(f)=f−$\gamma_B$(f) is called a white top-hat filter, whereas BTH(f)=$\varphi_B$(f)−f is called a black top-hat filter. The structural elements $\gamma_B$(f) and $\varphi_B$(f) are masks that are used to perform the basic morphological operation. The sizes of the structural elements vary slightly for cervical, thoracic, and lumbar applications. The empirical values are determined experimentally. The weighting coefficients w and b are determined adaptively by the amplitudes of WTH(f) and BTH(f), respectively. Empirically, the values of the weighting coefficients w and b have been found to be about 1 each (w=1, b=1), for a cervical case in which less tissue is present. In the lumbar case, in which more tissue is present, the values of w and b have been found to be greater than about 2 each (w>2, b>2). In the lumbar case, the weighting process brings out the skeletal structures to a greater degree, compared with the cervical case.

In one embodiment, image registration is conducted only in a certain region of interest (ROI) defined in the DRR. The ROI contains the treatment target (e.g. a tumor or lesion). In one embodiment, image entropy is specifically defined, in step 404 in FIG. 5. In this way, the ROI can be automatically selected, for optimum registration, minimizing or even eliminating user interaction. Because image registration relies on the image content or image information, in this embodiment the ROI is optimized to contain as much information as possible.

The Shannon entropy, known from conventional communication theory, is commonly used as a measure of information in signal and image processing. It is defined as $H=-\Sigma_i^n p_i \log p_i$, where H represents the average information supplied by a set of n symbols whose probabilities are given by $p_1, p_2, \ldots, p_n$. When applied to the pixels of each image (as enhanced in steps 403 or 415 in FIG. 5), the Shannon entropy for each image is defined by: $H=-\Sigma_I p(I) \log p(I)$, where I is the image intensity level, and p(I) is the probability of an image intensity value I occurring within the ROI. In the original formulation by Shannon, any change in the data that tends to equalize the probabilities $p_1, p_2, \ldots, p_n$ increases the entropy, as observed by Shannon. For a given image, the Shannon entropy is conventionally calculated from a image intensity histogram, in which the probabilities $p_1, p_2, \ldots, p_n$ are histogram entries.

In one embodiment, the Shannon entropy H is modified, based on the fact that the skeletal structures occur in bright areas. In this embodiment, a modified Shannon entropy is used for each image, which is defined as follows:

$$H=-\Sigma_I I p(I) \log p(I), \quad (3)$$

where again I is the image intensity level, and p(I) is the probability of the image intensity value I occurring within the ROI. In step 404 (shown in FIG. 5), the modified Shannon entropy is first determined for the enhanced DRR image. Once the modified Shannon entropy H is calculated, an ROI is then automatically selected by determining the region within the DRR for which the entropy H is maximized. Subsequent steps in the image registration process (steps 420-450 in FIG. 5) take place only within the ROI.

Restricting the image registration process to within a ROI has several advantages. One advantage is that such a restriction can speed up the registration process, since the registration needs to be performed only for the ROI. For example, the similarity measure needs only be computed for the ROI, and block matching need only be performed within the ROI. Further, the registration process is more accurate when limited to an area within the ROI. The more limited the region in which registration is conducted, the less likely it is that structures within the ROI would have moved relative to each other between the time of the pre-operative CT scans and the time of the medical treatment.

Based on the improved and enhanced DRRs (generated in steps 402 and 403 in FIG. 5), and the enhanced x-ray projection images (step 415 in FIG. 5), in which the skeletal reference structures have been brought out to make fiducial-less tracking possible, a non-rigid deformation of the anatomical region is determined in steps 420-450. In this patent, a 'rigid body' assumption, i.e. which is often made in image registration applications, and which assumes that between image acquisitions, the anatomical and pathological structures of interest do not deform or distort, does not have to be made. If a rigid body assumption is not needed, there is no longer a need to preserve the 'rigid body' constraints, i.e. to require that the body be rigid and not undergo any local variations during the transformation. Based on an abundance of observations and analyses on clinical patient data, in the present patent a non-rigid deformation is assumed, in lieu of a rigid transformation, to obtain an improved description of the real patient movement and body deformation. By computing a non-rigid deformation field, patient position/orientation can be more reliably monitored and corrected during the initial alignment, as well as throughout the entire treatment.

A non-rigid image registration allows the inherent local anatomical variations that exist between different image acquisitions to be accounted for, in contrast to a rigid image registration which does not allow the overcoming of such variations. Non-rigid registration defines a deformation field that provides a translation or mapping for every pixel in the image. In one embodiment, a full motion field, composed of many local motion vectors or fields, is computed in order to derive the non-rigid deformation field.

In order to estimate local motion fields, in one embodiment, a multi-level block matching method is used in conjunction with a similarity measure based on pattern intensity. This approach allows the local motion to be rapidly and accurately estimated in most parts of the ROI. Multi-level block matching, which allows for computational efficiency, is described in conjunction with a rigid registration algorithm, in a commonly owned application, U.S. Ser. No. 10/652,786 (the "'786 application"), incorporated by reference in its entirety. A similarity measure based on pattern intensity, used in conjunction with a registration algorithm based on rigid transformations, i.e. the "FAST 6D algorithm" developed by Accuray, Inc. for use with the Cyberknife radiosurgery system, is described in full in commonly owned applications, U.S. Ser. No. 10/652,786 (the "'786 application"), Ser. No. 10/652,717 (the "'717 application"), and Ser. No. 10/652,785 (the "'785 application"), which are all incorporated by reference in their entireties. In the present patent, the pattern intensity based similarity measure and the multi-level block matching method are used in conjunction with a registration algorithm based on a non-rigid (rather than a rigid) transformation. The pattern intensity-based similarity measure, originally developed for a rigid image registration algorithm, provides a powerful and efficient technique for solving the 2D/3D image registration problem, also in a non-rigid framework.

In one embodiment, block matching is performed, i.e. a small block centered around a point of interest is used in order to locally estimate the displacements at each desired point within the ROI. As known, when using block matching to register a first image onto a second image, the first image is divided into different blocks, typically rectangular boxes of equal size. Each point of interest, which may be a mesh node, or may be a non-node pixel that is surrounded by mesh nodes, is taken as the center of one of the blocks. These blocks are then translated so as to maximize a local similarity criterion, which in one embodiment is the pattern intensity based similarity measure, described above.

In block matching methods, it is generally assumed that each pixel in a block has the same motion, and a block matching algorithm is typically used to estimate the motion vectors for each block. In a block matching algorithm used in one embodiment, a search is conducted for a matching block in the second image, in a manner so as to maximize a measure of similarity, based on pattern intensity, between the respective blocks. The search is for a location of the maximum in the similarity measure function, the maximum representing the existence of a matching block in the second image. The search may be conducted within a search window that is defined around the point of interest and that contains the block.

In any block matching algorithm, it is important to optimize the search strategy, and to select an appropriate block size. For small blocks, the translational rigid model is typically assumed. Even though rigid rotations or some other complicated deformations exist, the rigid body translation model is valid for estimating the translations for the block center point. When rotations or other deformations exist in addition to the translations, the accuracy increases with decreasing block size, and decreases with increasing block size. With the use of smaller block sizes, however, the possibility of mismatching increases. In one embodiment, a block size selection strategy is adopted in which it is assumed that larger blocks are needed for larger displacements, and that smaller blocks are need for smaller displacements.

Figure 6:
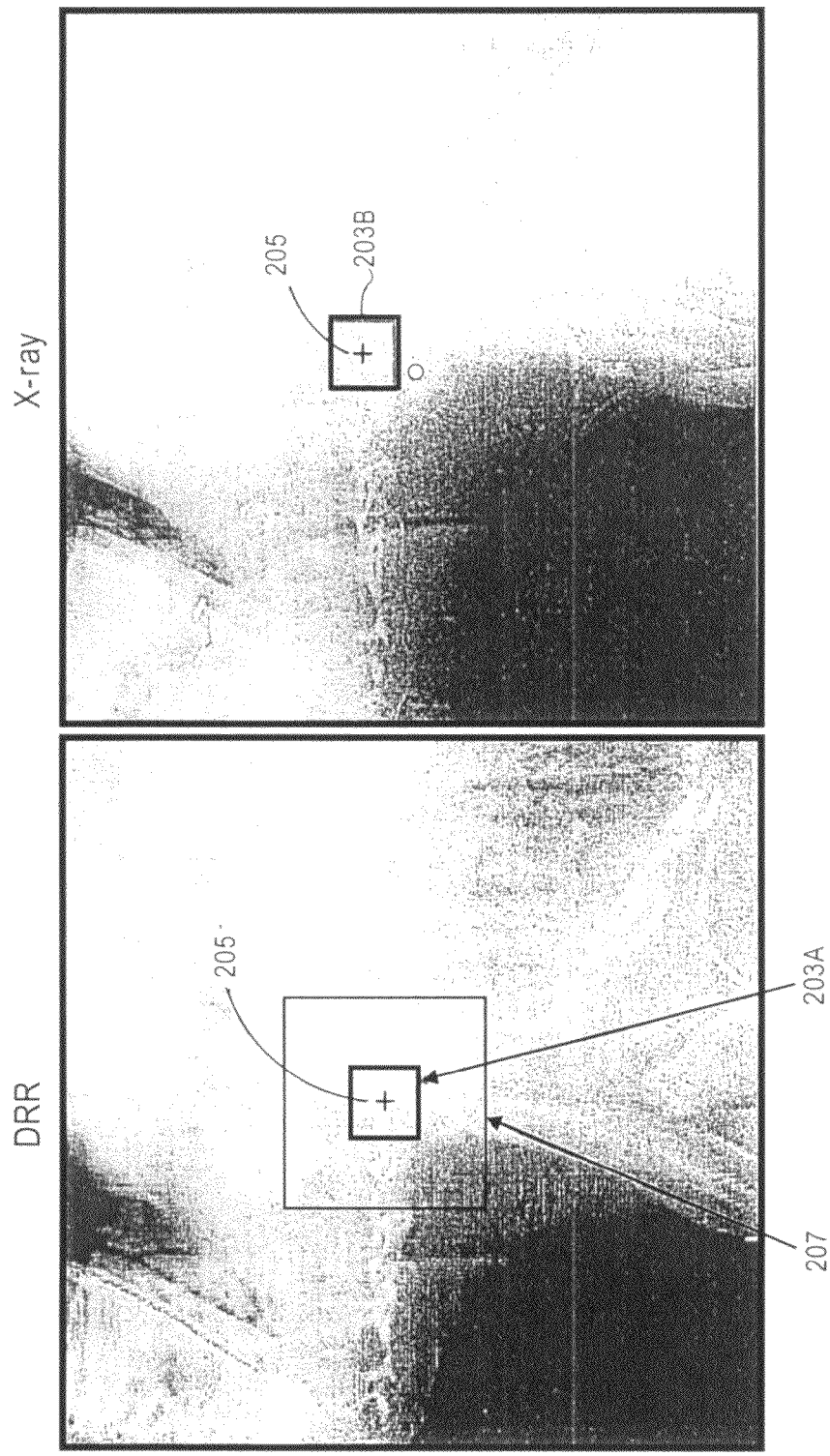
FIG. 6 schematically illustrates the use of block matching when estimating local motion for a point of interest within a target in a patient.

FIG. 6 schematically illustrates local motion estimation for a point of interest within a target in a patient, using block matching. In the embodiment illustrated in FIG. 6, the target is located in the cervical region of the spine, although it is again emphasized that the non-rigid 2D/3D image registration technique can be used in applications other than structural spine tracking. The left and the right pictures are the DRR and the x-ray images, respectively. A small block 203A is defined around a point of interest 205 in the DRR. Also, a search window 207 that encompasses the block 203 is defined in the DRR. The matching block in the x-ray image is indicated in FIG. 6 with reference numeral 203B. In the embodiment illustrated in FIG. 6, the size of the search window 207 is 48 mm×48 mm, and the block size is 15×15 mm. It can be seen, simply by visual inspection, that the point of interest 205 is well located in the X-ray image.

Figure 7:
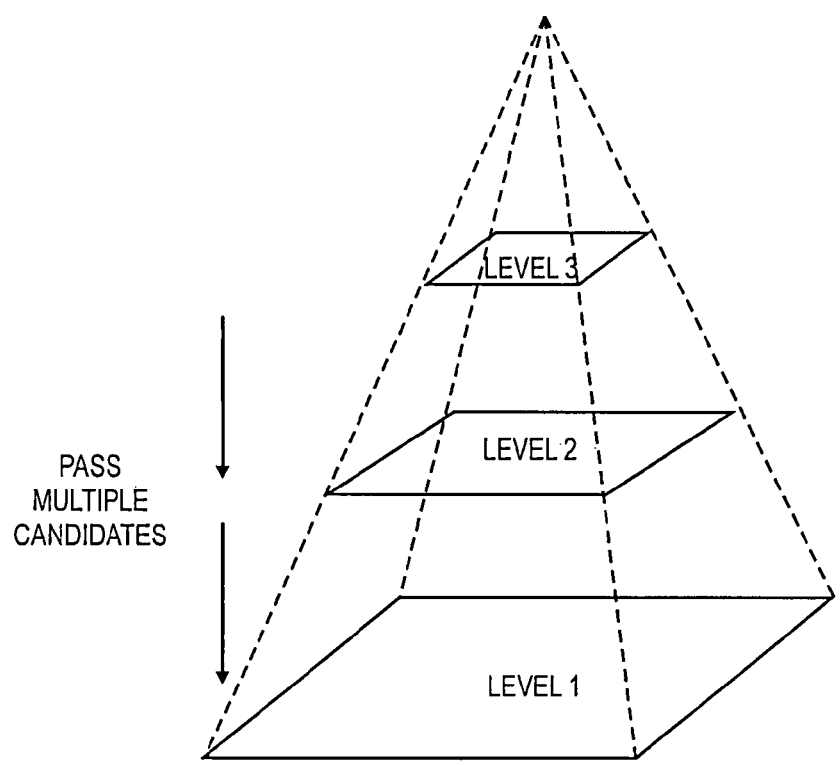
FIG. 7 schematically illustrates a multi-resolution image representation, for implementing multi-level block matching in one embodiment, using multiple candidates.

FIG. 7 schematically illustrates a multi-resolution image representation, when implementing multi-level block matching, using multiple candidates. Multi-level block matching is a fast search method that uses the displacement estimates made at a lower level as the initial results for subsequent search phases. The basic idea in multi-level block matching is to match the images at each of a plurality of resolution levels, successively, starting from the lowest resolution level and moving up to the highest resolution level. The full-size image, having the highest resolution level, is shown at the bottom in FIG. 7, as level 1. The upper images (level 2 and level 3) have successively lower spatial resolutions, the image having the lowest resolution being shown as level 3. The lower resolution images are obtained by lower pass filtering, and subsampling the full-size images.

In FIG. 7, assuming that the full image block size is W×H in Level 1, the block sizes are $$\frac{W}{2} \times \frac{H}{2} \text{ and } \frac{W}{4} \times \frac{H}{4}$$

in Level 2 and Level 3, respectively, as indicated in the figure. In the lowest resolution level (Level 3), a large search range is used to enable estimation of large displacements. A very small search range (−2, +2) is used in the rest of the resolution levels.

The results at the lower resolution level serve to determine rough estimates of the displacements. The output at the lower level is then passed onto the subsequent higher resolution level. The estimated motion vector (in most cases, a translation vector) for the block is successively refined, using the higher resolution images. In the final matching results, the accuracy of the estimated translations depends on the spatial resolution of the highest resolution images (shown as level 1 in FIG. 7).

There is some risk in multi-level matching. It is possible that the estimate at lower levels may fall in a local maximum, and far away from the global maximum that is being sought. In this case, further matchings at subsequent higher resolution levels may not converge to its global maximum. To overcome this risk, multiple candidates are used for the estimates, in one embodiment. Many candidates that have shown optimal matching results are passed on from the lower levels to the higher resolution levels. The more candidates that are used, the more reliable are the estimates. In one embodiment, the best candidates are ranked by the similarity measure function values.

In one embodiment, a similarity measure based on pattern intensity is used, in conjunction with multi-level block matching. As mentioned earlier, this similarity measure is a key element contributing to the success of the "FAST 6D algorithm," described in the commonly owned '786 application, '717 application, and '785 application. In one embodiment, the similarity measure is determined by forming a difference image between the "live" (or near real time) x-ray projection images and the DRR images, and applying upon each pixel of the difference image a pattern intensity function. Specifically, the difference image $I_{diff}(i,j)$ is formed by subtracting a corresponding pixel value of the pre-operative DRR image from each pixel value of the intra-operative x-ray projection image, within the ROI:

$$I_{diff}(i,j) = I_{Live}(i,j) - I_{DRR}(i,j) \quad (4)$$

In equation (4), I(i,j) represents the image intensity value of a pixel located at the i-th row and j-th column of each pixel array for the respective image. Specifically, $I_{diff}(i, j)$ represents an array of pixel values for a difference image formed by subtracting the corresponding pixel values of the second image from each pixel value of the first image. $I_{live}(i,j)$ represents the (i,j)-th pixel value of the first image of the object. $I_{DRR}(i,j)$ represents the (i,j)-th pixel value of the second image of the object. The similarity measure operates on this difference image, and is expressed as the summation of asymptotic functions of the gradients of the difference image over the pixels within a neighborhood R:

$$\sum_{i,j} \sum_{k,l \in R} \frac{\sigma^2}{\sigma^2 + (I_{diff}(i, j) - I_{diff}(i+k, j+l))^2} \quad (5)$$

In equation (5) above, the constant σ is a weighting coefficient for the pattern intensity function. The sensitivity of the solution to the variation of x-ray image can be minimized by careful selection of this constant. The larger the weighting coefficient, the more stable the results. However, the choice of σ entails a tradeoff between stability and accuracy. When the value of σ is too large, some small details in the images cannot be reflected in the similarity measure. Based on the experiments, the empirical value for σ is in the range from about 4 to about 16, in one embodiment.

Figure 8:
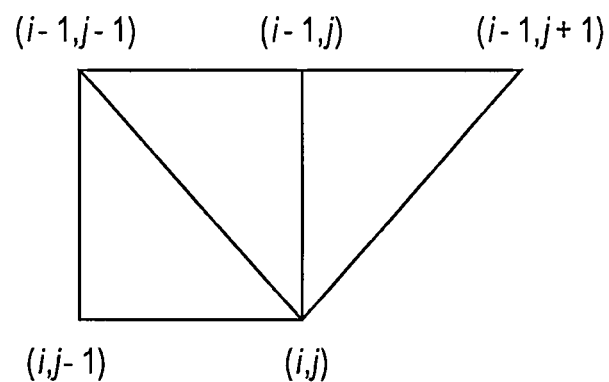
FIG. 8 schematically illustrates a neighborhood R for calculating a similarity measure based on pattern intensity.

FIG. 8 schematically illustrates a neighborhood R for calculating a similarity measure based on pattern intensity. As seen from FIG. 8, the neighborhood R in the illustrated embodiment is defined so that the gradients of the difference image can be considered in at least four directions (horizontal, vertical, 45° diagonal and −45° diagonal). When the neighborhood R is defined in this manner, equation (5) for the similarity measure becomes:

$$\sum_{i,j} \frac{\sigma^2}{\sigma^2 + ((I_{diff}(i,j) - I_{diff}(i,j-1))^2} + \qquad (6)$$

$$\sum_{i,j} \frac{\sigma^2}{\sigma^2 + ((I_{diff}(i,j) - I_{diff}(i-1,j))^2} +$$

$$\sum_{i,j} \frac{\sigma^2}{\sigma^2 + ((I_{diff}(i,j) - I_{diff}(i-1,j-1))^2} +$$

$$\sum_{i,j} \frac{\sigma^2}{\sigma^2 + ((I_{diff}(i,j) - I_{diff}(i-1,j+1))^2}.$$

Equations (5) and (6) for pattern intensity have several advantages. First, the difference image filters out the low frequency part that predominantly consists of the soft tissues, and keeps the high frequency part that predominantly consists of the skeletal structures. This feature makes the algorithm robust to some brightness intensity difference between live and DRR images. Second, because of the asymptotic function, the measure is less affected by the pixels whose intensity value slightly deviates from its neighboring pixels. These types of pixels are thought to contain random noise. Third, because the asymptotic function quickly approaches to zero when the variable increases, large intensity differences such as image artifacts have the same effects on the similarity measure regardless of their magnitude. Due to this feature, the pattern intensity is less sensitive to image artifacts.

The estimation of local motion fields using block matching together with hierarchical mesh motion estimation, as well as the reconstruction of the full motion field from the plurality of locally estimated motion fields, are performed in steps 420-450 of the flowchart shown in FIG. 5. Fast generation of the full motion field is achieved by using hierarchical mesh tracking, and using SIMD (single instruction multiple data) technology to perform image computation in parallel.

In one embodiment, a global translation of the entire image (measured as a translation of the image center of the image) is first estimated, then used as the initial estimates for all further local motion estimation. In other words, a rough estimate is made of the center displacement for the entire image, and is used as the starting estimate for all local displacements. Referring back to FIG. 5, the first step (indicated with reference numeral 420 in FIG. 5) in generating a full motion field for a target, between the pre-operative scan and the intra-operative treatment, is the step of estimating a global translation for the entire image, or equivalently, estimating the center displacement of the image.

Figure 9:
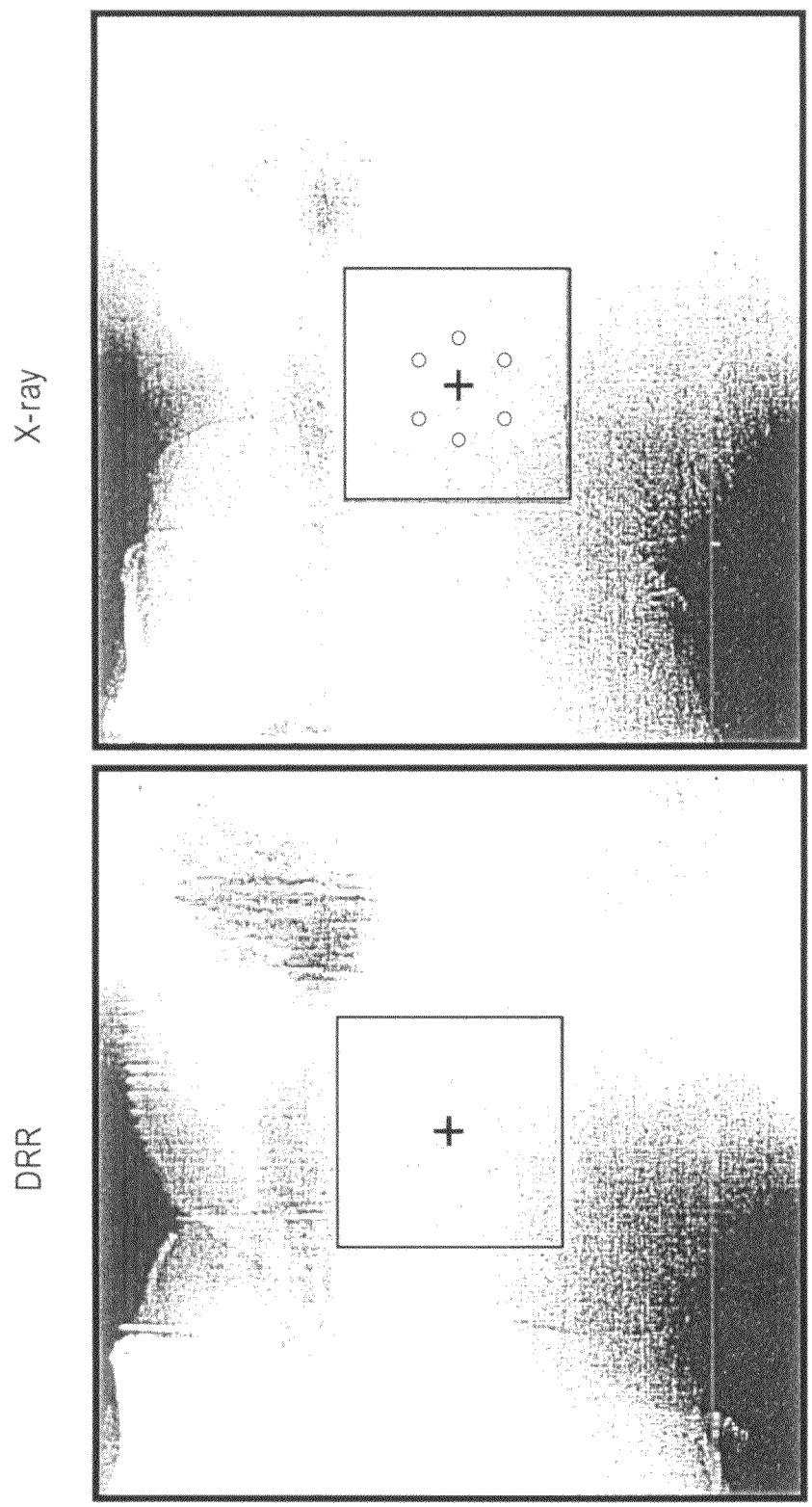
FIG. 9 illustrates the estimation of global translation, between the image center of a DRR and the image center of a corresponding x-ray image.

FIG. 9 illustrates the estimation of global motion (in this case, translation only), between the image center of a DRR and the image center of a corresponding x-ray image. In the illustrated embodiment, the image center is used as the block center. The step of global translation estimation is very important, because any failure during this step will affect the rest of the local motion estimation process. To prevent any possibility of mismatching, a very large image block is used in the illustrated embodiment. The maximum tracking range can be calculated as the difference between the block size and the entire image size. For example, if the matching size is 80×80 mm, the maximum tracked translation is 60 mm. In the embodiment illustrated in FIG. 9, a block having a size of 160×160 pixels (64 mm×64 mm) is used. The search window in the illustrated embodiment is the entire image. The maximum track range for the illustrated embodiment is (−50 mm, +50 mm).

After global motion estimation, the next step 430 (see FIG. 5) is mesh motion estimation. In this step, a hierarchical 2D mesh structure is designed in order to estimate local motion in multiple levels. As known, a 2D mesh (or a 2D mesh grid) refers to a tesselation of a 2D region into polygonal patches or elements, whose vertices are called mesh nodes. Unlike block matching algorithms, which generally assume only translational motion, 2D mesh models allow for spatial transformations to model rotations, scalings, and deformations of the object that was imaged, in addition to translations of the object. Compared to block matching algorithms, therefore, mesh-based methods may produce a more accurate representation of the motion field, for example may generate continuously varying motion fields.

Figure 10:
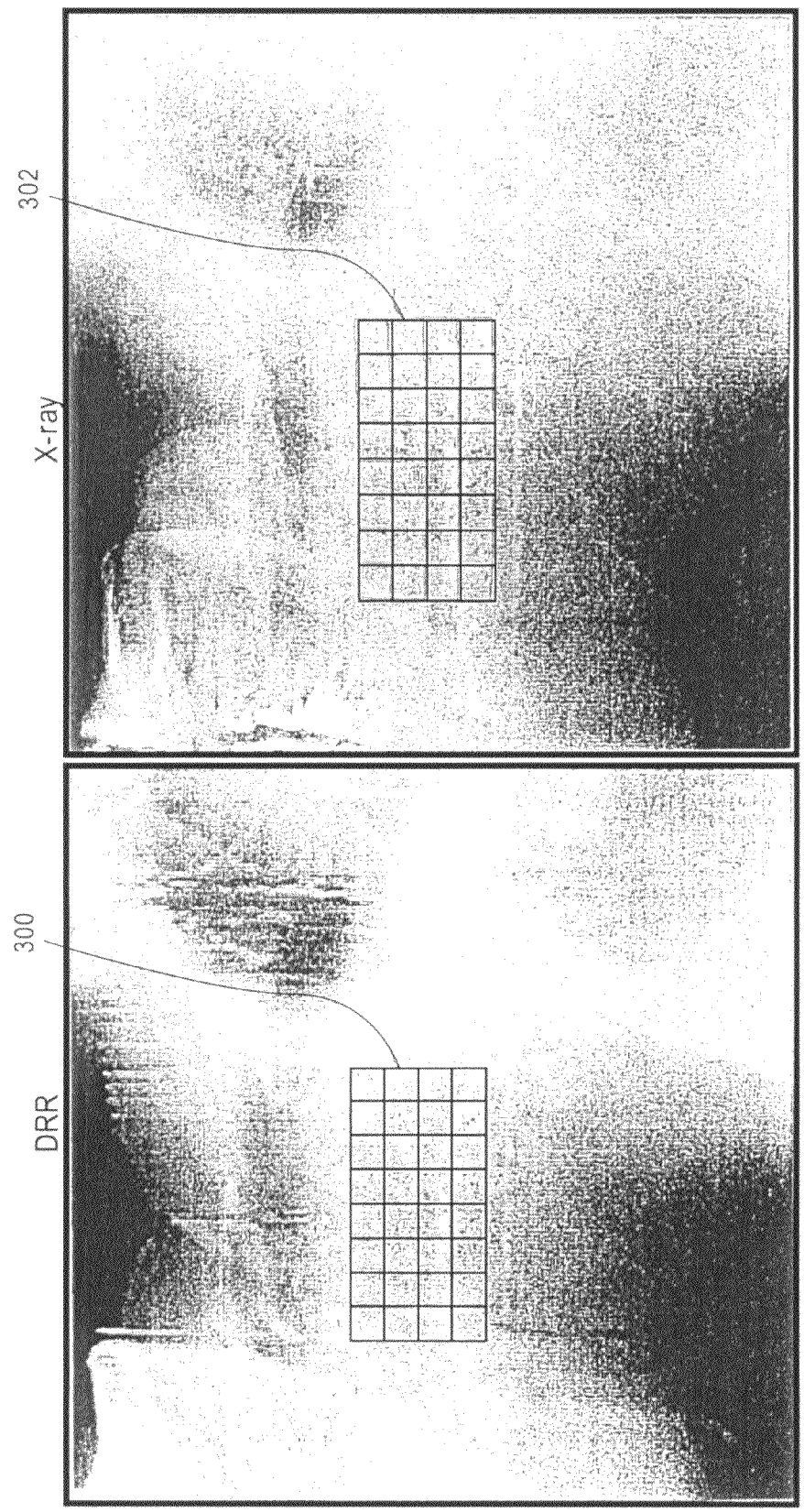
FIG. 10 schematically illustrates a mesh grid established for a DRR of a target, and a corresponding mesh grid established for an x-ray image of the target, in an embodiment in which the target is located within the cervical region of the spine.

FIG. 10 schematically illustrates a mesh grid 300 established for a DRR of a target region, and a corresponding mesh grid 302 established for an x-ray image of the target region, in an embodiment in which the target is located within the cervical region of the spine. With a 2D mesh, motion compensation within each mesh element or patch may be accomplished by deriving a spatial transformation between the images, where the transformation parameters are computed from the nodal motion vectors, i.e. from the motion vectors that are estimated for the mesh nodes that are located at the vertices of the mesh. In other words, mesh-based motion estimation consists of finding a spatial transformation that best maps one set of mesh elements in a first image acquisition onto another set of mesh elements in a second image acquisition.

In particular, mesh motion estimation consists of finding the vertices of corresponding mesh elements in the other image, i.e. finding the corresponding mesh nodes in the other image, such that errors are minimized in the overall motion field. Typically, a number of mesh nodes are selected in one image, and the corresponding mesh nodes in the other image are estimated. For any pixel located within a mesh element (as opposed to being located on the vertices of the mesh elements), the mapping between different image acquisitions is performed through interpolation. The local motion vectors for such pixels are estimated by interpolating from the nodal motion vectors that were estimated for the mesh nodes that surround the pixel.

In one embodiment, hierarchical mesh motion estimation may be performed. By hierarchical mesh motion estimation, it is meant that nodal motion is estimated for the mesh nodes that define the mesh structure, for each of a plurality of mesh resolution levels. Motion estimation performed with a coarse mesh provides the initialization for the subsequent (finer) resolution levels of the mesh. To estimate the motion of each mesh node, multi-level block matching may be performed.

Figure 11:
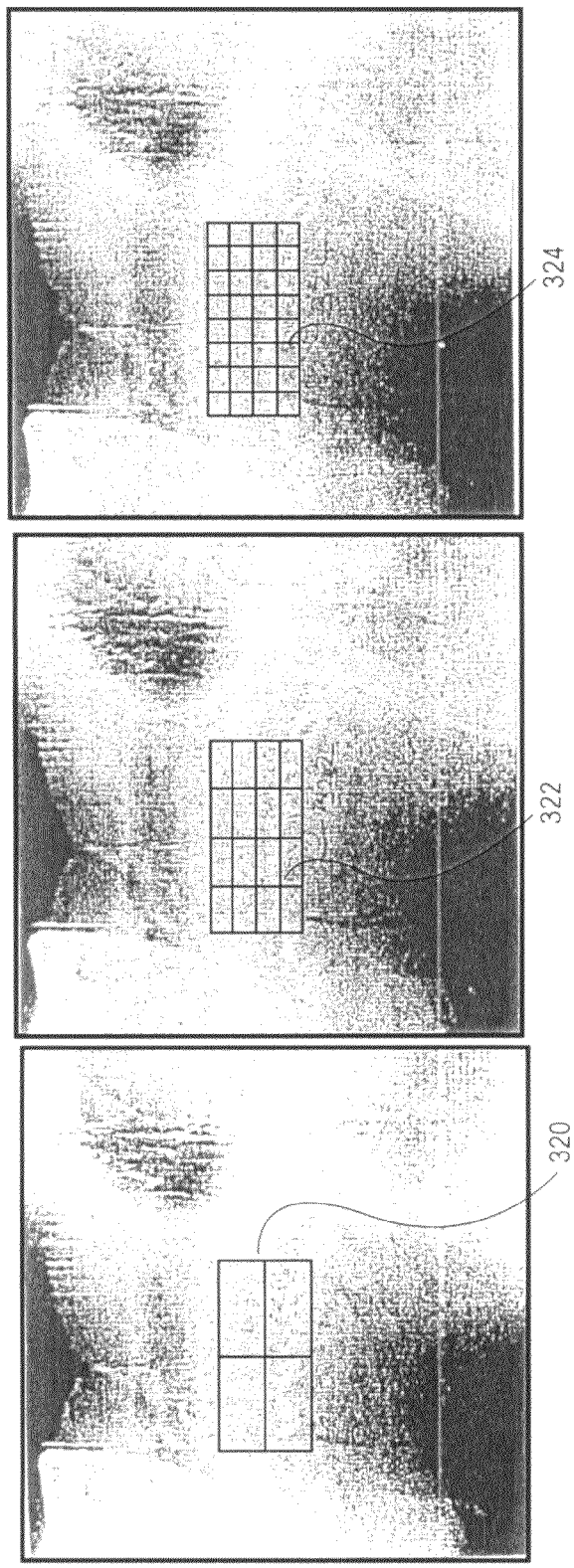
FIG. 11 illustrates a mesh hierarchy, during mesh motion estimation, the mesh hierarchy starting from a relatively coarse mesh, and progressing onto finer meshes.

FIG. 11 illustrates a mesh hierarchy, during mesh motion estimation. As seen from FIG. 11, the mesh hierarchy starts from a relatively coarse mesh, 320, and progresses onto finer meshes, illustrated as 322 and 324. Using the global translations (estimated in step 420 of FIG. 5 as the initial estimates), nodal motion for the mesh nodes located at the vertices of the most coarse mesh is first calculated. These estimates are then passed onto the subsequent, finer mesh. At each level, nodal motion is updated, using a smaller search range. Finally, the motion vectors for the mesh nodes at the final one of the mesh resolution levels (characterized by the finest mesh resolution level) are refined. For all the nodes, multi-level block matching with multiple candidates is used, together with the pattern-intensity based similarity measure, given in equations (5) and (6).

FIG. 12 schematically illustrates the passing on of node estimation, from a coarse mesh resolution level onto a finer mesh resolution level. At each mesh resolution level after the first level, the mesh nodes include both 1) mesh nodes generated at a previous mesh resolution level; and 2) mesh nodes that are newly added at the current mesh resolution level. In the illustrated embodiment, the initial estimates for nodal motion vectors, for the newly added nodes at the current mesh, are obtained by linear interpolation of the existing nodal motion vectors, at the previous mesh resolution level. During this process, any unreliable mesh node needs to be detected, so that only reliable nodes are passed onto the subsequent mesh level.

FIG. 12 illustrates how such a detection can be performed, using a mesh node referred to in FIG. 12 as 'node 5.' In the illustrated embodiment, the difference between the motion vector (in this case, translation vector) of node 5, and the median motions (translations) computed from its 9 surrounding nodes (nodes 1-4, 6-9 in FIG. 12) is taken. As seen from FIG. 12, the translation of node 2 is the average of the translations of node 1 and node 3; the translation of node 4 is the average of the translations of node 1 and node 7; the translation of node 6 is the average of the translations of node 3 and node 9; and the translation of node 8 is the average of the translations of node 7 and node 9. The translation of node 5 is the average of the translations of nodes 1, 3, 7, and 9. If the difference between the translation of node 5 and the median translations computed from its 9 neighboring nodes is less than a predefined threshold, the node 5 is considered as a reliable node. Otherwise, it is considered as an unreliable node, and its translations are replaced with the median values and passed to the subsequent mesh.

For most mesh nodes, the estimates of motion are reliable and accurate. For a few nodes where mismatching may occur and the estimation may not be reliable, the displacements need to be reconstructed by the surrounding node displacements. Accordingly, the next step in the registration algorithm flow chart in FIG. 5 is step 440 of motion field reconstruction, during which the motion field is reconstructed from surrounding nodes, for those nodes in which mismatching occurs. The inaccurate nodal motion vectors can be detected by using 3×3 median filtering.

Local motion estimation relies on the local image content. In some smooth local regions, mismatching may occur. During mesh motion estimation, the estimation in most nodes is pretty accurate. For a few nodes where mismatching occurs, the motions should be reconstructed from their surrounding nodes. What is known a priori is matter coherence of bone and tissue, and accordingly, the smoothness of local motion. In other words, the estimated local motion vectors are thought to be smooth and continuous, because of matter coherence. By imposing this physically-based smoothness constraint, a cost function is formulated to reconstruct the motion field.

In one embodiment, the cost function is expressed mathematically as follows:

$$E(d) = \iint \beta(d-u)^2 dx dy + \lambda \iint (d_x^2 + d_y^2) dx dy \quad (7)$$

In equation (7) above, E(d) represents the cost function, d represents a desired local estimate for a nodal motion vector at coordinates (x,y), u represents a locally estimated nodal motion vector at coordinates (x,y), and β represents a reliability constant that ranges from 0 to 1, where β=0 indicates an unreliable estimation, and β=1 indicates a reliable estimation.

By performing a finite difference of the derivatives over the mesh grids, a discretized form for the cost function in equation (7) is expressed as:

$$E(d_{i,j}) = \Sigma\Sigma \beta_{i,j}(d_{i,j} - u_{i,j})^2 + \lambda \Sigma\Sigma[(d_{i,j} - d_{i-1,j})^2 + (d_{i,j} - d_{i,j-1})^2] \quad (8)$$

where $u_{i,j}$ represents the locally estimated translations, $d_{i,j}$ is the local motion desired, $\beta_{i,j}=1$ if the estimation is reliable and $\beta_{i,j}=0$ if the estimation is unreliable.

The first term on the right side of equation (8) reflects the fidelity to the observed data in the reconstruction. The second term imposes the smoothness constraints on the motion field in two spatial directions.

The minimization of the cost function given by equation (8) results in a system of simultaneous linear equations $$\frac{\delta E(d_{i,j})}{\partial d_{i,j}} = (\beta_{i,j} + 4\lambda)d_{i,j} - \lambda(d_{i-1,j} + d_{i+1,j} + d_{i,j-1} + d_{i,j+1}) - \beta_{i,j}u_{i,j} = 0 \quad (9)$$

In one embodiment, the iterative algorithm of successive-over relaxation (SOR), which is fast and convergent, is used to solve the equations:

$$d_{i,j}^{(n+1)} = d_{i,j}^{(n)} - \omega[(\beta_{i,j}+4\lambda)d_{i-1,j}^{(n)} - \lambda(d_{i-1,j}^{(n)} + d_{i+1,j}^{(n)} + d_{i,j-1}^{(n)} + d_{i,j+1}^{(n)}) - \beta_{i,j}u_{i,j}]/(\beta_{i,j}+4\lambda) \quad (10)$$

Figure 13:
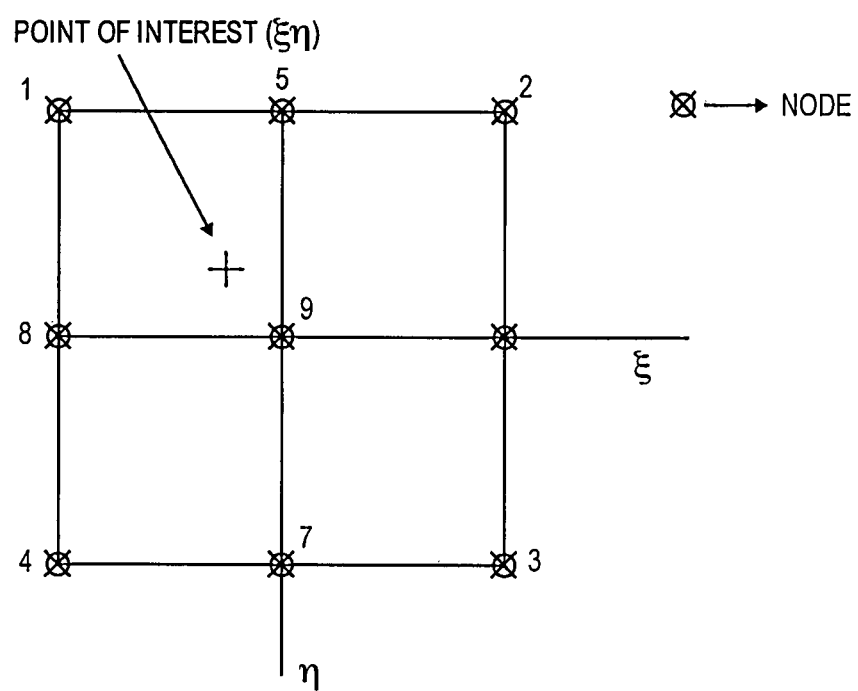
FIG. 13 schematically illustrates the determination of a motion vector for a point of interest, by interpolation from surrounding nodes.

Once all the nodal motion vectors have been estimated at all the mesh nodes, the translations for any point (or pixel) inside the ROI can be computed by interpolation. FIG. 13 schematically illustrates the determination of a motion vector for a point of interest, by interpolation from surrounding nodes. In the illustrated embodiment, quadratic interpolation is performed, using the 9 nearest nodes, and 9 shape functions are used.

Assuming the motion vector (dx(i), dy(i)) for nine nodes, the motion vector (dx, dy) at the point of interest is computed using the following expressions:

$$dx = \sum_{i=1}^{9} N(i) dx(i), \quad (11)$$

$$dy = \sum_{i=1}^{9} N(i) dy(i),$$

where N(i) is the shape function for the node (i), and where N(i) for I=1, 2, . . . 9 are given as follows:

$$N(1) = (1-\xi)(1-\eta)/4 - (N_8 + N_5)/2,$$

$$N(2) = (1-\xi)(1-\eta)/4 - (N_5 + N_6)/2,$$

$$N(3) = (1+\xi)(1+\eta)/4 - (N_6 + N_7)/2,$$

$$N(4) = (1-\xi)(1+\eta)/4 - (N_7 + N_8)/2,$$

$$N(5) = (1-\xi^2)(1-\eta)/2,$$

$$N(6) = (1-\xi)(1-\eta^2)/2,$$

$$N(7) = (1-\xi^2)(1+\eta)/2,$$

$$N(8) = (1-\xi)(1-\eta^2)/2,$$

$$N(9) = (1-\xi^2)(1-\eta^2). \quad (12)$$

Figure 14:
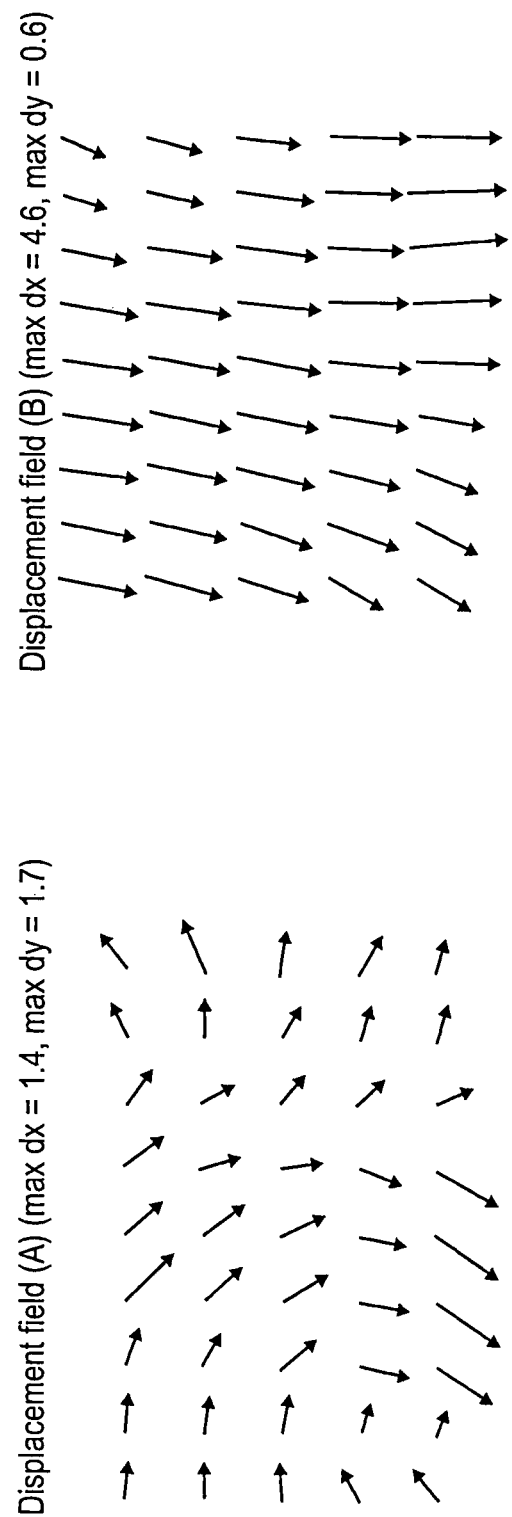
FIG. 14 schematically illustrates, in vectorial form, a full motion field reconstructed from many estimated local motion vectors.

Using steps 420, 430, and 440, described above, the local motion vectors can be estimated for a plurality of points of interest within the ROI. The full motion field is obtained as a composite or superposition of all of the local motion vectors that are estimated for the many points of interest that have been selected for motion estimation. FIG. 14 schematically illustrates, in vectorial form, a full motion field (reconstructed from many estimated local motion vectors), in an embodiment in which the target is located within the cervical region of the spine.

The final step in the image registration process is target localization, namely deriving the target translations and rotations from the full motion field that has been determined. In one embodiment, non-rigid image registration seeks to determine a projection mapping or transformation between different coordinate systems in respective image acquisitions such that points in each space which correspond to the same anatomical point are mapped to each other. In one embodiment, the transformation is represented by a set of non-rigid transformation parameters $(dx_T, dy_T, dz_T, r, p, w)$, where $(dx_T, dy_T, dz_T)$ represent the translations of the target, and $(r, p, w)$ represent rotations of the target.

In one embodiment, two orthogonal x-ray projections are used to solve for these six parameters. In this embodiment, the registration in each projection is performed individually, and the results of the registration for each projection are subsequently combined, to obtain the six 3D transformation parameters. In other embodiments, however, different projections or combinations thereof may be used to solve for the transformation parameters.

Figure 15:
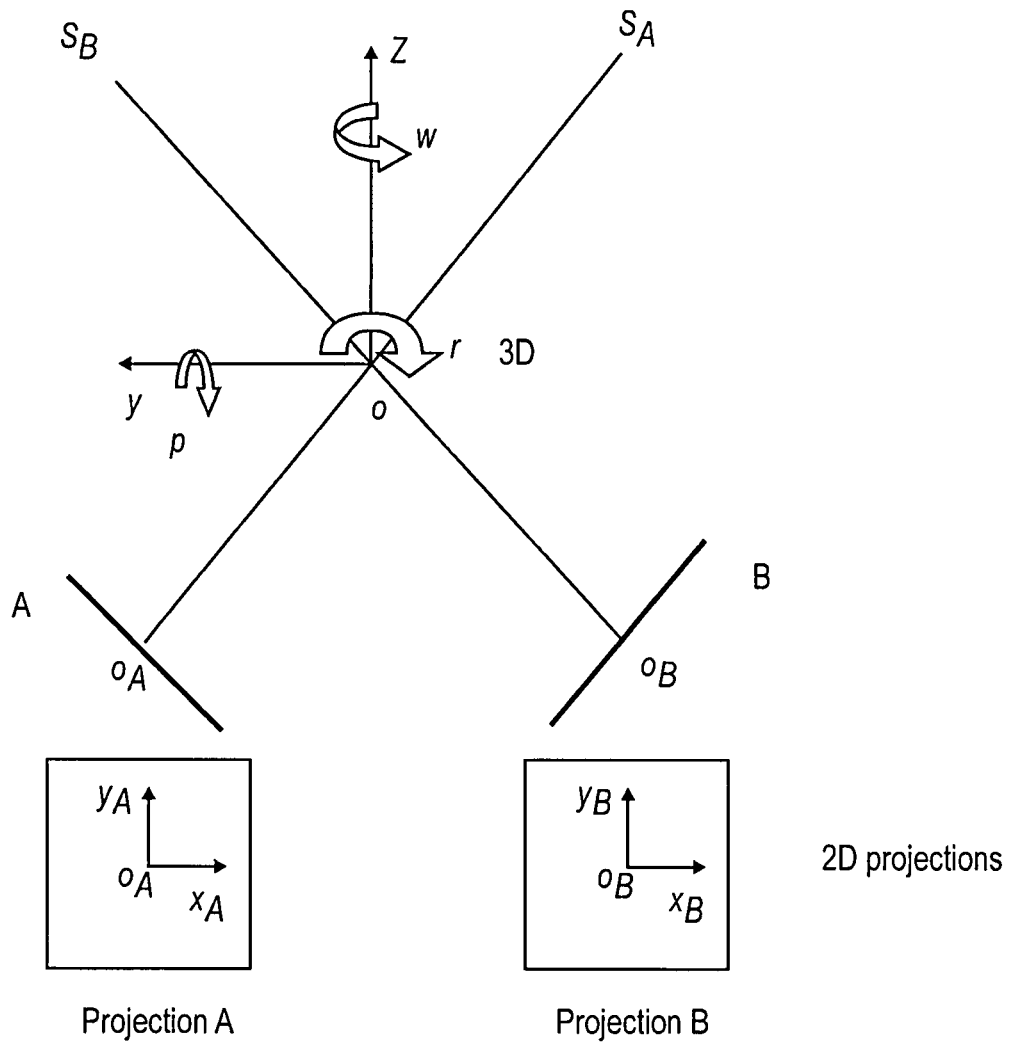
FIG. 15 illustrates the geometric relations between a three-dimensional treatment target, and two orthogonal 2D x-ray projections FIG. 16 schematically illustrates dynamic tracking of a moving target within a patient during real time delivery of treatment radiation, using surface markers (e.g. LEDs) to monitor the breathing motion of the patient.

FIG. 15 illustrates the geometric relations between a three-dimensional treatment target, and two orthogonal 2D x-ray projections (labeled A and B in FIG. 15), in a non-rigid image registration method in accordance with one embodiment. A pair of cameras (or image receivers) A and B receive their x-ray projections from respective x-ray sources (not shown). In the coordinate system of the 3D scan, the x-axis is directed inward into the paper, and is not indicated in FIG. 15. As explained above, the change in position of the treatment target is represented by three translations and three global rigid rotations (dx, dy, dz, r, p, w).

In FIG. 15, the orthogonal 2D projections A and B are viewed from the directions $o_A s_A$ and $o_B s_B$, respectively. For each of the projections A and B, FIG. 15 illustrates respective 2D planar coordinate systems that are fixed with respect to the image plane that characterizes each projection. The image planes A and B for the projections A and B are thus defined by mutually orthogonal axes within the respective coordinate systems. These axes are shown in FIG. 15 as $(x_A, y_A)$ for projection A, and $(x_B, y_B)$ for projection B. The direction of the axis $x_A$ in the 2D coordinate system for projection A, and the direction of the x-axis in the 3D scan coordinate system, are opposite with respect to each other. The direction of axis $x_B$ in the coordinate system for projection B, and the direction of the axis x in the 3D scan coordinate system, are the same.

For projection A, the 2D motion field $(dx_A, dy_A)$ is estimated by registering the x-ray image that is projected onto the image plane A, with the corresponding reference DRR image. For projection B, the 2D motion field $(dx_B, dy_B)$ is estimated by registering the x-ray image that is projected onto the image plane B, with the corresponding reference DRR image. Given the 2D motion fields $(dx_A, dy_A)$ for projection A, and $(dx_B, dy_B)$ for projection B, the 3-D target translation $(dx_T, dy_T, dz_T)$, as well as the global rigid rotations $(r, p, w)$, can be obtained for both projections A and B, by a straightforward mathematical operation.

Referring back to FIG. 5, the 3-D target translation $(dx_T, dy_T, dz_T)$ can easily be obtained in step 455 (shown in FIG. 5), given the 2D local motion fields $(dx_A, dy_A)$ for projection A, and $(dx_B, dy_B)$ for projection B, using the following expressions:

$$dx_T = (dx_{TA} + dx_{TB})/2,$$

$$dy_T = (dy_{TA} - dy_{TB})/\sqrt{2},$$

$$dz_T = (dy_{TA} + dy_{TB})/\sqrt{2} \quad (13)$$

The global rigid rotations (r, p, w) can be calculated from the motion fields $(dx_A, dy_A)$ in projection A and $(dx_B, dy_B)$ in projection B. Using the target as the rotation center, global rigid rotations are useful for position and rotation correction and compensation during initial patient alignment and treatment. Because the target translation is already calculated, the calculation of the global translation is not needed. To get the three rotations in 3D patient coordinates, three 2D in-plane rotations are first computed, including the in-plane rotations $\theta_A$ and $\theta_B$ in projections A and B, respectively, and the in-plane rotation $\theta_x$ in a plane perpendicular to the inferior-superior axis. Approximately, the global rotations can be expressed as:

$$r = \theta_x,$$

$$p = (\theta_B - \theta_A)/\sqrt{2},$$

$$w = (\theta_B + \theta_A)/\sqrt{2}, \quad (14)$$

Estimation of $\theta_A$ and $\theta_B$ is directly based the 2D motion fields in projections A and B, respectively. To estimate $\theta_x$, a plane is first defined, which passes the target point and is perpendicular to the axis x in the 3D patient coordinate system. Then the motion field is calculated from the two motion fields $(x_A, y_A)$ and $(x_B, y_B)$ in projections A and B, respectively.

Assuming (dx, dy) is the motion field in the corresponding coordinate (x, y) and $\theta$ is the global rotation, when the rotation is small (<10°), the following transformation equation is valid:

$$\begin{Bmatrix} dx \\ dy \end{Bmatrix} = \begin{bmatrix} 0 & -\theta \\ \theta & 0 \end{bmatrix} \begin{Bmatrix} x \\ y \end{Bmatrix} \quad (15)$$

Given (dx,dy) and (x,y) in many points, $\theta$ can be easily calculated using least square minimization method $$\theta = \frac{\sum_i (x(i)dy(i) - y(i)dx(i))}{\sum_i (x(i)x(i) + y(i)y(i))} \quad (16)$$

Using equations (14) and (16) above, the average rigid transformation parameters can be obtained, in step 160 illustrated in FIG. 5.

Figure 16:
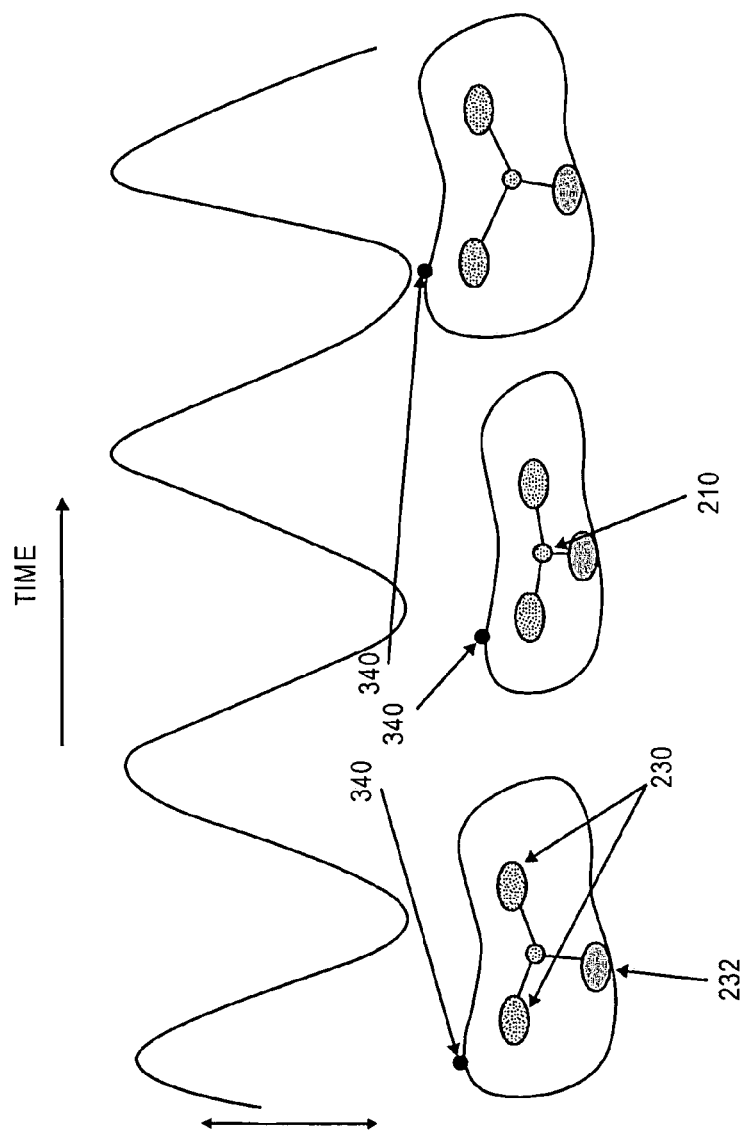

Using the results of non-rigid registration, obtained as described above, dynamic tracking of the targets can be performed during treatment delivery, by using the 4D mathematical model, and by monitoring the breathing (or other motion) cycle during delivery of radiation. FIG. 16 schematically illustrates dynamic tracking of a moving target within a breathing patient during delivery of treatment radiation, using surface markers 340 (e.g. infrared LEDs) to monitor the breathing motion of the patient as a function of time.

Although surface markers are described with respect to the embodiment illustrated in FIG. 16, in other embodiments other techniques may be used to track the surface of the patient. These techniques include, but are not limited to: video systems; laser scanners; ultrasound (or other acoustic) scanners; and when tracking heartbeat motion, electrocardiograms. Any method and device known in the art to track patient surfaces may be used.

Dynamic tracking of the target 210 (i.e. the tumor/lesion 210) during treatment delivery can achieved by combining the 4D mathematical model obtained during 4D treatment planning, with the registration information provided by fiducial-less tracking, and monitoring of the patient breathing motion using surface markers. As explained above, the 4D mathematical model obtained during treatment planning relate the locations of the skeletal structures 230 and 232 to the locations of the target 210.

A number of approaches to dynamic tracking are possible, when using fiducial-less tracking in association with 4D planning and dynamic tracking of surface markers, as schematically shown in FIG. 16. In a first approach, the surface markers 340 are first used to determine the instant in the breathing cycle. The rigid reference structures 232 can then be located, using non-rigid fiducial-less tracking. The location of the tumor/lesion 210 is then tracked, by drawing vectors from the reference locations determined using non-rigid image registration. The knowledge of the instant in the breathing cycle, obtained using the surface markers 340, and the models obtained from 4D treatment planning that relate the locations of the target 210 to the locations of the rigid skeletal structures 232, are used to draw vectors from the rigid reference structures 232 whose locations have been obtained during non-rigid image registration.

In a second approach, the tumor/lesion 210 is located, using the location of the reference structures 232 and 230 obtained from fiducial-less tracking, and using a model that relates the location of the reference structures 232 and 230 to the lesion 210, obtained from 4D treatment planning. Next, a mathematical model is built that relates the motion of the surface markers 340 to the motion of the lesion 210. In image processing, it is known in the art to relate the motion of a first type of object with the motion of a second type of object, and to describe such a relation in terms of a mathematical model. Algorithms or software that are known and that may be commercially available can be used to built the mathematical model that relates the motion of the surface markers 340 to the motion of the lesion 210.

In a third approach, the locations of the reference structures that are determined from the 4D model obtained during 4D treatment planning are used to locate the lesion by interpolation. A mathematical model is then built that relates the motion of the surface markers 340 to the motion of the lesion 210. This third approach involves the least dependence on the 4-D planning model obtained from treatment planning.

In a final approach, the tumor or lesion 210 is directly tracked, using the 2D/3D registration techniques described in the above paragraphs. In this approach, the model relating the motion of surface markers to the location of the target 210 can be built directly, using just the results of the 2D/3D registration.

Once the targets have been located, using one of the approaches described above, radiation beam delivery can be implemented. The real time locations of the targets within the moving anatomical region, which are determined as described in the previous paragraphs, provide guidance for beam delivery. During treatment planning, the beam trajectories are initially defined with respect to a nominal patient co-ordinate system, perhaps chosen to orient with respect to one of the several CT studies acquired to cover the motion cycle. This epoch in the motion cycle is determined by analyzing the motion of the surface markers, and each radiation beam is to be turned on from this epoch.

Figure 17:
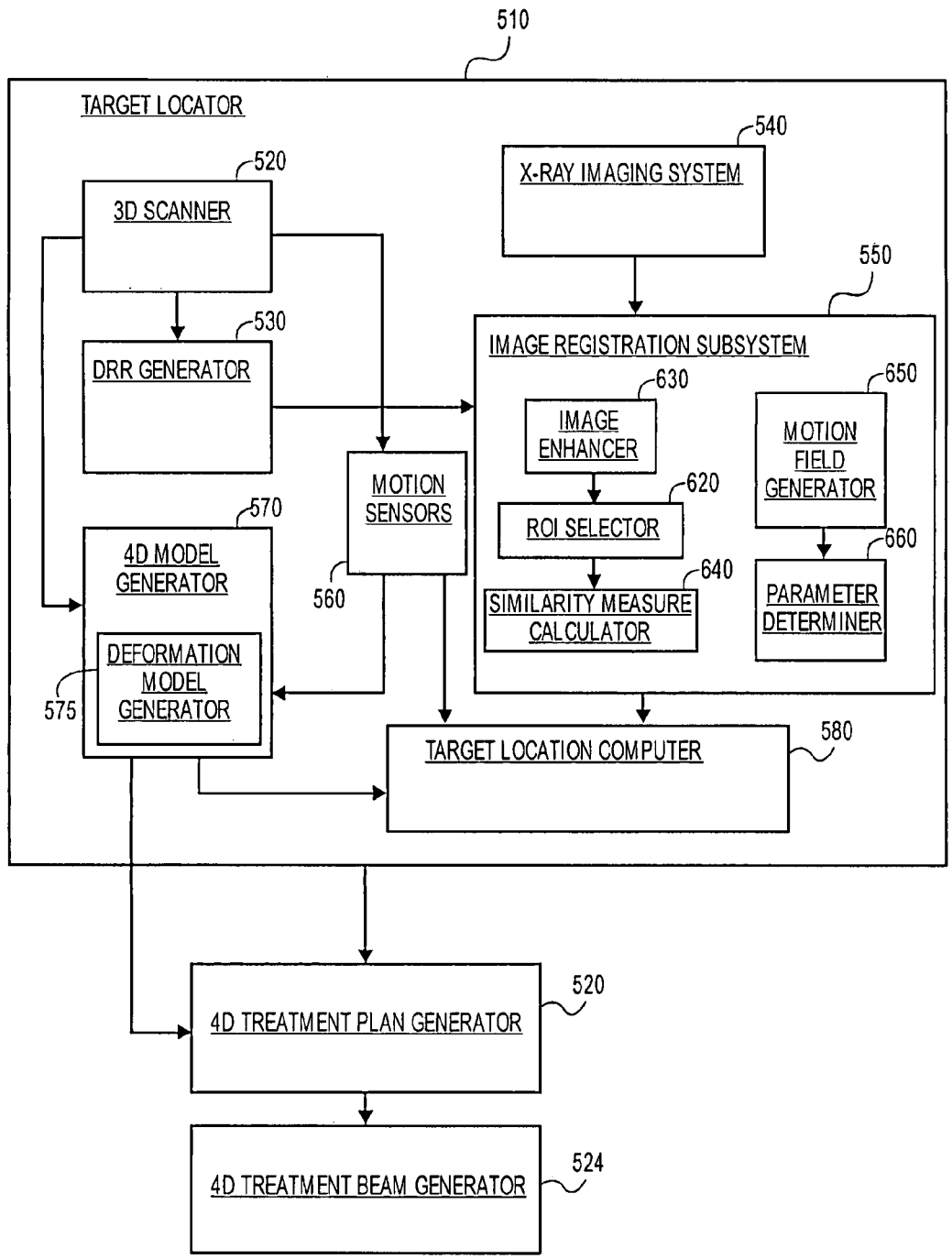
FIG. 17 provides a schematic block diagram of a system for dynamically tracking targets within an anatomical region that is undergoing periodic motion (e.g. respiration or heartbeat) and delivering therapeutic radiation to the moving targets.

FIG. 17 provides a schematic block diagram of an apparatus 500 for dynamically tracking targets 210 within an anatomical region that is undergoing periodic motion having a cycle P, and for delivering therapeutic radiation to the moving targets. The targets may include tumors or lesions. The anatomical region includes reference structures in addition to the targets 210. The reference structures may include rigid reference structures 232 which do not move during the periodic motion, and reference structures 230 which themselves move during the periodic motion of the anatomical region.

In overview, the apparatus 500 includes: a target locater 510 that determines in real time the locations of the target(s) 210 relative to the reference structures 230 or 232 within the periodically moving anatomical region; a 4D treatment planning generator 520 that generates a 4D treatment plan as a function of the relative position in time within P for the moving anatomical region; and a treatment beam generator 524 that delivers therapeutic radiation to the targets in real time in accordance with the treatment plan. The treatment plan prescribes a desired radiation dose distribution to be delivered in real time to the targets, while accounting for a deformation of the moving anatomical region during the periodic motion. The treatment planning generator 520 may be connected to a treatment delivery controller (not shown) which controls the delivery of radiation, in accordance with the treatment plan generated by the treatment planning generator 520.

Also included may be a robot system (not shown), which typically has a fixed base and an articulated arm assembly at the distal end of which the treatment beam generator (e.g. x-ray source such as a linac) may be mounted. The robot system may move (and orient), in response to the directions of the delivery controller, the treatment beam generator (i.e. x-ray linac). The robot system and treatment beam generator are described in detail, for example in commonly owned U.S. Pat. No. 5,207,223, and U.S. patent application Ser. No. 10/814,451 both incorporated by reference herein in their entireties.

In one embodiment, the target locater 510 includes a 3D scanner 520; a DRR generator 530; an x-ray imaging system 540; an image registration subsystem 550; one or more motion sensors 560; a 4D model generator 570; and a target location computer 580. The 3D scanner 520 generates a plurality of 3D images $I_j$ (j=1, . . . , p) of the anatomical region, at each of a succession of time points $t_j$ (j=1, . . . , p) within the cycle P. These 3D images may include, but are not limited to: a 3D CT scan; a 3D MRI scan; a 3D PET (positron emission tomography) scan; and a 3D ultrasound scan. The 3D scanner 520 can therefore be one of: a 3D CT scanner; a 3D PET scanner; a 3D MRI scanner; and a 3D ultrasound scanner.

The time points $t_j$ (j=1, . . . , p) are preferably chosen to substantially encompass a full range of the periodic motion of the anatomical region. For example, the time points may include: a first time point corresponding to a peak of the cycle P, a second time point corresponding to a trough of the cycle P, and a third time point disposed at an intermediate location between the peak and the trough of the cycle P. The motion sensors 560, which may be surface markers, for example, monitor the periodic motion of the anatomical region, and measure the cycle P. In this way, the motion sensors 560 generate time position data representative of the relative position within P of one or more desired time points.

The DRR generator 530 reconstructs DRRs from the 3D scan data, at each time point $t_j$, by casting hypothetical rays through the volumetric 3D scan data from a known beam projection geometry, and integrating the 3D scan data along each ray. The x-ray imaging system 540 generates near real time 2D x-ray projection images of the targets 210 and the reference structures 230 and 232 within the moving anatomical region, by detecting x-ray imaging beams after the beams have traversed at least a portion of the anatomical region. These x-ray imaging beams are generated from the same beam projection geometry as used to generate the DRRs.

The image registration subsystem 550 registers the near real time x-ray projection images of the reference structures and/or the targets, with the DRRs of the reference structures and/or the targets, thereby determining the locations of the reference structures and/or the targets. In one embodiment, the image registration subsystem 550 includes: 1) an ROI selector 620 configured to select an ROI (region of interest) within the DRR, the ROI containing the treatment target and preferably at least one reference structure; 2) an image enhancer 630 configured to enhance the DRRs and the x-ray images by applying a filter operator to the DRR and to the x-ray image;
3) a similarity measure calculator 640 configured to determine a measure of similarity between the DRR and the x-ray image; 4) a motion field generator 650 configured to generate a 3D full motion field by estimating, for each of a plurality of resolution levels, one or more 2D local motion fields within the ROI, using the similarity measure; and
5) a parameter determiner 660 configured to determine a set of non-rigid transformation parameters that represent the difference in the position and orientation of the treatment target as shown in the x-ray image, as compared to the position and orientation of the treatment target as shown in the DRR, from the 3D full motion field.

The 4D model generator 570 generates a 4D model that describes a motion of the targets 210 relative to the reference structures 232 within the moving anatomical region, as a function of the relative position in time within the cycle P. The target location computer 580 computes the locations of the targets at the one or more desired time points. The target location computer 580 uses the 4D model constructed by the 4D model generator 570, to correlate the locations of the targets with the known locations of the reference structures, as determined by the image registration subsystem 550, and uses the time position data obtained by the motion sensors 560 to determine the relative position within P of each desired time point.

In one embodiment, the 4D model generator 570 includes a deformation model constructor 575 configured to construct a mathematical model that describes the deformation and motion of the anatomical region, as a function of the relative position in time within the cycle P. In this embodiment, the 4D model generator 570 derives the 4D model from the mathematical model constructed by the deformation model constructor 575. The deformation model constructor 575 extracts, from the plurality of images $I_j$ generated by the 3D scanner 520, deformation data that contain information relating to the deformation and motion of the anatomical region.

In one embodiment, the deformation model constructor 575 extracts the deformation data from the plurality of images by registering each image that is taken at a time point $t_j$ within P, onto a consecutive image that is taken at a consecutive time point $t_{j+1}$ within P. The information contained in the deformation data comprises information relating to the change in the position and orientation of the targets relative to the reference structures. The deformation model constructor 575 uses the deformation data, together with the time position data from the motion sensors 560 to mathematically correlate, for each time point $t_j$, the relative position within P of the time point $t_j$ with the deformation and motion of the targets at the time point $t_j$.

Using the 4D mathematical model generated by the 4D model generator 570, the results of non-rigid image registration as performed by the image registration subsystem 550, and the relative position in time within the breathing cycle as determined by the motion sensors 560, the target location computer 580 computes the locations of the tumors/lesions.

Using the 4D mathematical model generated by the 4D model generator 570, the 4D treatment plan generator 520 generates a desired radiation dose distribution that results from continuous radiation beam delivery through the non-rigidly moving anatomical region. Finally, the treatment beam generator 524 generates and treatment beams in accordance with the desired radiation dose distribution, and delivers them in real time to the targets.

In sum, a number of techniques have been described for dynamically tracking tumors/lesions in the anatomy that move, for example due to periodic motion such as respiration. These techniques combine 4D treatment planning, fiducial-less tracking of skeletal structures or targets, and dynamic tracking of surface markers with pertinent mathematical models, to achieve dynamic tracking of the tumors/lesions of interest.

While the invention has been particularly shown and described with reference to specific embodiments, it should be understood by those skilled in the art that many modifications and variations in form and detail may be made in the techniques and structures described and illustrated herein, without departing from the spirit and scope of the invention. Accordingly, the techniques and structures described and illustrated herein should be understood to be illustrative only and not limiting upon the scope of the present invention. The scope of the present invention is defined by the claims, which includes known equivalents and unforeseeable equivalents at the time of filing of this application.

What is claimed is:

1. A method of dynamically tracking one or more targets within an anatomical region and delivering therapeutic radiation to the one or more targets, while the anatomical region undergoes a periodic motion characterized by a motion cycle P, the anatomical region comprising one or more internal anatomical reference structures, the method comprising:

monitoring, based on one or more surface markers configured for attachment to an external surface of the anatomical region, the periodic motion to measure the cycle P;

generating near real time images of the one or more targets and the one or more internal anatomical reference structures within the moving anatomical region;

determining, in real time, locations, within the moving anatomical region, of the one or more targets relative to the one or more internal anatomical reference structures based on a) registering the near real time images to one or more digitally reconstructed radiographs (DRRs) generated from pre-operative images in which the one or more internal anatomical reference structures were identified and b) applying an outcome of the registration to a 4D mathematical model that describes a non-rigid deformation of the anatomical region, as a function of time within the cycle P, and which describes a 3D motion of the one or more targets relative to the one or more internal anatomical reference structures as a function of the time within the cycle P; and delivering, based on the determined locations, the therapeutic radiation in real time to the one or more targets as the anatomical region undergoes the periodic motion.

2. A method in accordance with claim 1, wherein the determining in real time of the locations of the one or more targets relative to the one or more internal anatomical reference structures comprises:

constructing the 4D mathematical model;

determining the real time locations of the one or more internal anatomical reference structures at each of a plurality of time points $t_i$, i=1, ..., N, by registering the near real time images of the one or more internal anatomical reference structures with the one or more DRRs of the pre-operative images, and monitoring the periodic motion of the anatomical region to determine relative position of time within the cycle P of each time point $t_i$; and computing the real time locations of the one or more targets at each time point t, using locations of the one or more internal anatomical reference structures from the near real time images and determined positions within the cycle P of each time point $t_i$.

3. A method of dynamically tracking one or more targets within an anatomical region and delivering therapeutic radiation to the one or more targets, while the anatomical region undergoes a periodic motion characterized by a cycle P, the anatomical region comprising an internal anatomical reference structure, the method comprising:

constructing a 4D mathematical model that describes a non-rigid deformation of the anatomical region, and a 3D motion of the one or more targets relative to the internal anatomical reference structure, as a function of the time within the cycle P;

using the 4D mathematical model to generate a desired dose distribution for delivery of therapeutic radiation to the one or more targets;

dynamically tracking the periodic motion of the anatomical region, based on one or more external motion sensors configured for attachment to at least a portion of an outer surface of the anatomical region, to determine the relative position of time within the cycle P of time points;

registering one or more near real time images of the internal anatomical reference structure with one or more digitally reconstructed radiographs (DRRs) generated from pre-operative images of the internal anatomical reference structure to derive the real time locations of the internal anatomical reference structure;

using the real time locations of the internal anatomical reference structure, the 4D model, and knowledge of the determined relative position of time within the cycle P of the desired time points, computing the real time locations of the one or more targets; and delivering therapeutic radiation to the real time locations of the one or more targets, in accordance with the desired dose distribution.

4. A method of dynamically tracking, and delivering therapeutic radiation to, one or more targets within an anatomical region of a patient while the patient undergoes a periodic motion characterized by a cycle P, the anatomical region comprising an internal anatomical reference structure, the method comprising:

constructing from pre-operative scan data of the one or more targets a 4D mathematical model that describes a non-rigid deformation of the anatomical region as a function of time within the cycle P, and describes a 3D motion of the one or more targets relative to the internal anatomical reference structure;

generating from the 4D mathematical model a radiation dose distribution for delivering therapeutic radiation onto the one or more targets throughout the cycle P;

performing non-rigid image registration of near real time 2D images of the internal anatomical reference structure with digitally reconstructed radiographs (DRRs) generated from pre-operative 3D scans of the internal anatomical reference structure;

determining the relative position within the cycle P of at least one time point, using one or more tracking devices attached to at least a portion of an outer surface of the anatomical region;

computing in real time the locations of the one or more targets at the at least one time point, using results of the non-rigid image registration and the 4D mathematical model; and delivering therapeutic radiation to the real time locations of the one or more targets at the at least one time point within the cycle P, in accordance with the desired dose distribution.

5. A method in accordance with claim 4, wherein the tracking device comprises at least one of:
a laser scanner;
a video system;
an ultrasound scanner; or
an electrocardiogram.

6. An apparatus for dynamically tracking one or more targets within a moving anatomical region in order to deliver therapeutic radiation to the one or more targets, the anatomical region comprising one or more internal anatomical reference structures and undergoing a motion characterized by a periodic cycle P, the apparatus comprising:

one or more motion sensors, configured for attachment to at least a portion of an outer surface of the anatomical region, to enable the periodic motion of the anatomical region to be sensed and to enable a relative position in time within the periodic cycle P of one or more desired time points to be identified;

an x-ray imaging system configured to generate near real time 2D x-ray projection images of the one or more targets and the one or more internal anatomical reference structures within the moving anatomical region;

a target locater to determine in real time the locations of the one or more targets relative to the one or more internal anatomical reference structures within the periodically moving anatomical region, wherein the target locator comprises:

an image registration subsystem configured to register the near real time x-ray projection images of the one or more internal anatomical reference structures with digitally reconstructed radiographs (DRRs) generated from preoperative images of the one or more internal anatomical reference structures, thereby determining the locations of the one or more internal anatomical reference structures; and a target location computer configured to compute in real time the locations of the one or more targets at the one or more desired time points, by using a 4D mathematical model to correlate the locations of the one or more targets with the known locations of the one or more internal anatomical reference structures, as determined by the image registration subsystem, and by using the time position data to determine the relative position within the periodic cycle P of each desired time point; and a 4D treatment planning generator to generate a 4D treatment plan as a function of time for the one or more targets in the moving anatomical region, the treatment plan prescribing a desired radiation dose distribution to be delivered in real time to the one or more targets, and accounting for a deformation of the moving anatomical region during the motion.

7. An apparatus in accordance with claim 6,
wherein the target locater comprises:
a 3D scanner configured to generate the preoperative images, the preoperative images comprising 3D scan data comprising a plurality of 3D images $I_j$ (j=1, ..., p) of the anatomical region, at each of a succession of time points $t_j$ (j=1, ..., p) within the cycle P;
a DRR generator configured to reconstruct the DRRs from the volumetric 3D scan data, at each time point $t_j$, by casting hypothetical rays through the volumetric 3D scan data and integrating the volumetric 3D scan data along each ray; and
a 4D model generator configured to generate a 4D mathematical model that describes a motion of the one or more targets relative to the one or more internal anatomical reference structures within the moving anatomical region, as a function of time within the cycle P.

8. An apparatus in accordance with claim 7,
wherein the 4D model generator comprises a deformation model constructor configured to construct a mathematical model that describes the deformation and motion of the anatomical region as a function of the position in time within the cycle P;
wherein the deformation model constructor is configured to extract, from the plurality of 3D images $I_j$ generated by the 3D scanner, deformation data that contain information relating to the deformation and motion of the anatomical region; and
wherein the deformation model constructor is configured to use the deformation data and the time position data to mathematically correlate, for each time point $t_j$ the relative position within the cycle P of the time point $t_j$ with the deformation and motion of the one or more targets at the time point $t_j$.

9. An apparatus in accordance with claim 6, wherein the motion of the anatomical region comprises respiration, and the cycle P comprises a respiratory cycle.

10. An apparatus in accordance with claim 6, wherein the one or more motion sensors comprise a breathing sensor.

11. An apparatus in accordance with claim 6, wherein the motion of the anatomical region comprises a heartbeat, the cycle P comprises a heartbeat cycle, and the one or more motion sensors comprise a heartbeat monitor.

12. An apparatus in accordance with claim 7, wherein the plurality of 3D images taken at the time points $t_j$ comprise at least one of: a 3D CT scan, a 3D magnetic resonance imaging (MRI) scan, a 3D positron emission tomography (PET) scan, and a 3D ultrasound scan.

13. An apparatus in accordance with claim 6, further comprising a treatment beam generator configured to deliver therapeutic radiation to the one or more targets in real time in accordance with the radiation dose distribution, while the anatomical region undergoes the periodic motion.

14. An apparatus in accordance with claim 6, wherein the one or more motion sensors comprise at least one of:
a surface marker;
a laser scanner;
a video system;
an ultrasound scanner; or
an electrocardiogram.

15. An apparatus in accordance with claim 7, wherein the time points $t_j$ (j=1, ..., p) are chosen to substantially encompass a full range of the periodic motion of the anatomical region.

16. An apparatus in accordance with claim 15, wherein the time points comprise at least: a first time point corresponding to a peak of the cycle P, and a second time point corresponding to a trough of the cycle P.

17. An apparatus in accordance with claim 8, wherein extracting the deformation data from the plurality of 3D images comprises:
registering each image that is taken at a time point $t_j$ within P, onto a consecutive image that is taken at a consecutive time point $t_{j-1}$ within P.

18. An apparatus in accordance with claim 8, wherein information contained in the deformation data comprises information relating to a change in a position and orientation of the one or more targets relative to the one or more internal anatomical reference structures.

19. An apparatus in accordance with claim 6, wherein the one or more targets comprise at least one of a tumor or a lesion, and wherein the one or more internal anatomical reference structures comprise skeletal structures.

20. An apparatus in accordance with claim 7, wherein the 3D scanner comprises at least one of a 3D CT scanner, a 3D positron emission tomography (PET) scanner, a 3D magnetic resonance imaging (MRI) scanner, or a 3D ultrasound scanner.

21. An apparatus for dynamically tracking one or more targets within an anatomical region in order to deliver therapeutic radiation to the one or more targets, the anatomical region including one or more reference structures and undergoing a periodic motion characterized by a cycle P so that relative positions between the one or more targets and the one or more reference structures change periodically with time, the apparatus comprising:
a 3D scan data generator to generate volumetric 3D scan data, at each of a succession of time points $T_j$ within the cycle P;
one or more motion sensors coupled to the scan data generator to generate output signals representative of the relative position in time within the cycle P of each time point $T_j$, so that the 3D scan data generator can be activated at pre-selected positions in time within the cycle P;
a DRR generator to reconstruct DRRs, at each time point $T_j$, from the 3D scan data by casting hypothetical rays through the volumetric 3D scan data and integrating the 3D scan data along each ray;
a 4D treatment planning processor to generate a treatment plan as a function of the relative position in time within the cycle P for the moving anatomical region, in which the relative positions between the one or more targets and the one or more reference structures change periodically with time, the treatment plan representing a desired dose distribution of therapeutic radiation to be delivered to the one or more targets as the anatomical region undergoes the periodic motion;
wherein the 4D treatment planning processor is configured to generate, in response to receipt of the DRRs at each time point $T_j$, parameters $P_j$ representative of a non-rigid deformation of the anatomical region, as shown in the DRR generated at $T_j$, when compared to the DRR generated at $T_{j-1}$, and to describe in a mathematical model these parameters $P_j$ as a function of the relative position in time within the cycle P of the time point $T_j$, an x-ray imaging system to generate near real time 2D x-ray projection images of the one or more reference structures within the anatomical region;

an image registration processor to register the near real time x-ray projection images with the DRRs, so that near real time locations of at least one of the one or more reference structures or the one or more targets can be determined throughout the periodic motion of the anatomical region;

a treatment beam generator to generate, when activated, one or more beams having a strength sufficient to generate a therapeutic effect on the one or more targets;

one or more surface markers, configured for attachment to at least a portion of the outer surface of the anatomical region, to sense the periodic motion of the anatomical region and to generate output signals representative of the relative position in time within the cycle P of one or more desired time points; and a controller coupled to the treatment beam generator, wherein responsive to the outputs of the 4D treatment planning processor, the image registration processor, and the one or more surface markers, the controller is to activate the treatment beam generator so as to deliver one or more beams of therapeutic radiation to the one or more targets in accordance with the desired dose distribution, while the anatomical region undergoes the periodic motion.

* * * * *